US009884854B2

(12) United States Patent
Riether et al.

(10) Patent No.: US 9,884,854 B2
(45) Date of Patent: Feb. 6, 2018

(54) N-[(PYRIMIDINYLAMINO)PROPANYL]-AND N[(PYRAZINYLAMINO)PROPPANYL] ARYLCARBOXAMIDES

(71) Applicant: Boehringer Ingelheim International GmbH, Ingelheim am Rhein (DE)

(72) Inventors: Doris Riether, Biberach an der Riss (DE); Marco Ferrara, San Donato Milanese (IT); Niklas Heine, Biberach an der Riss (DE); Uta Friederike Lessel, Maselheim (DE); Janet Rachel Nicholson, Oberhöfen (DE); Anton Pekcec, München (DE); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/485,262

(22) Filed: Apr. 12, 2017

(65) Prior Publication Data
US 2017/0298053 A1 Oct. 19, 2017

(30) Foreign Application Priority Data

Apr. 15, 2016 (EP) ..................................... 16165538

(51) Int. Cl.
*C07D 413/12* (2006.01)
*C07D 403/04* (2006.01)
*C07D 401/14* (2006.01)
*C07D 401/12* (2006.01)

(52) U.S. Cl.
CPC ......... *C07D 413/12* (2013.01); *C07D 401/12* (2013.01); *C07D 401/14* (2013.01); *C07D 403/04* (2013.01)

(58) Field of Classification Search
None
See application file for complete search history.

(56) References Cited

FOREIGN PATENT DOCUMENTS

| EP | 2862855 A1 | 4/2015 |
|----|------------|--------|
| WO | 03051872 A1 | 6/2003 |
| WO | 2016034882 A1 | 3/2016 |

OTHER PUBLICATIONS

International Search Report and Written Opinion, PCT/ISA/220, dated May 26, 2017, for PCT/EP2017/058318.

*Primary Examiner* — Heidi Reese
(74) *Attorney, Agent, or Firm* — Marc Began; Usha R. Patel

(57) ABSTRACT

The present invention relates to novel N-[(Pyrimidinylamino)propanyl]- and N-[(Pyrazinylamino)-propanyl] arylcarboxamide derivatives, processes for their preparation, pharmaceutical compositions containing them and their use in therapy, particularly in the treatment or prevention of conditions having an association with the orexin sub-type 1 receptor.

4 Claims, No Drawings

N-[(PYRIMIDINYLAMINO)PROPANYL]-AND N[(PYRAZINYLAMINO)PROPPANYL] ARYLCARBOXAMIDES

FIELD OF THE INVENTION

The present invention relates to novel N-[(Pyrimidinylamino)propanyl]- and N-[(Pyrazinylamino)-propanyl] arylcarboxamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more).

Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8): e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders, such as borderline personality disorder, eating disorders such as binge eating disorder or attention deficit hyperactivity disorder. Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO03/051872, WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-[(Pyrimidinylamino)propanyl]- and N-[(Pyrazinylamino)-propanyl] arylcarboxamide derivatives that unexpectedly are highly potent OX1R antagonists (assay A) further characterized by
1) high selectivity over the OX2 receptor (assay B),
2) a medium to high stability in human liver microsomes (assay C), and
3) no or low MDCK (Madin-Darby canine kidney) efflux (assay D).

Compounds of the present invention are superior to those disclosed in the prior art in terms of the combination of the following key pharmacodynamic and pharmacokinetic parameters:
1) potency as OX1R antagonists,
2) selectivity over the OX2 receptor,
3) stability in human liver microsomes, and
4) MDCK efflux.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro. Enhanced stability in human liver microsomes is associated with several advantages, including increased bioavailability and longer half-life, which can enable lower and less frequent dosing of patients. Thus, enhanced stability in human liver microsomes is a favorable characteristic for compounds that are to be used for drugs.

The MDCK assay provides information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1 P-gp. Identical or similar permeabilities in both transport directions indicate passive permeation, vectorial permeability points to additional active transport mechanisms. Higher PEBA than PEAB (PEBA/PEAB>5) indicates the involvement of active efflux mediated by MDR1 P-gp, which might compromises the goal to achieve sufficient brain exposure. Therefore this assay provides valuable support for selection of compounds applicable for further in vivo testing. High permeability not limited by efflux at the blood brain barrier is a favourable characteristic for compounds that are to be used for drugs acting primarily in the CNS Compounds of the present invention are though encompassed by formula I of WO03/051872, differ structurally from those explicitly disclosed therein in that 1) they contain a central N-ethyl-(propan-2-yl)amino moiety in place of the N-methyl-ethylamino, NH-ethylamino, or NH-(propan-2-yl)amino moiety, and
2) the left hand side moiety consists of a phenyl, pyridyl, pyrazyl or pyrimidyl group further substituted with a heteroaryl group in place of a thiazolyl group further substituted with a phenyl group. These structural differences unexpectedly result in higher potency, higher selectivity over the OX2R and enhanced stability in human liver microsomes than the structurally closest example explicitly disclosed in WO03/051872.

Compounds of the present invention differ structurally from those disclosed in WO2013/187466 in that they contain a (5-trifluoromethyl-pyrimidin-2-yl)-amino or (5-trifluoromethyl-pyrazin-2-yl)-amino moiety in place of a Het1-Het2 moiety in which Het2 is phenyl or pyridyl. These structural differences unexpectedly result in a higher selectivity over the OX2R and enhanced stability in human liver microsomes.

Compounds of the present invention differ structurally from Examples 91, 84, 90, 40, 73, 46 and 14 in WO2016/034882 (the closest prior art compounds) in that they contain a central N-ethyl-(propan-2-yl)amino moiety in place of the N-ethyl-[butan-2-yl]amino or N-methyl-[propan-2-yl]amino moiety. These structural differences unexpectedly result in a superior combination of the following key pharmacodynamic and pharmacokinetic parameters:
1) potency as OX1R antagonists,
2) selectivity over the OX2 receptor,
3) stability in human liver microsomes, and
4) MDCK efflux.

Due to their high potency at OX1R and selectivity over OX2R, compounds of the present invention are expected to be both efficacious in in vivo models and to have a sufficient window between efficacy and undesired effects such as drowsiness or sleep.

Due to the superior combination of the key pharmacodynamic and pharmacokinetic parameters (#1-4) compounds of the present invention are expected to demonstrate adequate brain exposure and to have a medium to low in vivo clearance and thus a longer duration of action and higher tolerability. Consequently, compounds of the present invention must be more viable for human use.

GENERAL DEFINITIONS

Terms not specifically defined herein should be given the meanings that would be given to them by one skilled in the art in light of the disclosure and the context.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z-isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid. Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

BIOLOGICAL ASSAYS

Abbreviations

IP1 D-Myo-Inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO Chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:

A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 μL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM, and/or 50 nM) dissolved in assay buffer is added to the assay plate. The assay plate is incubated for 60 minutes at 37° C. Then 5 µl per well of Anti-IP1-Cryptate Tb solution and 5 µl per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader. 8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx2 cell mass is expanded to larger cell numbers. The cells are obtained as frozen cells in cryo-vials and stored until use at $-150°$ C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 µL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay. On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM) dissolved in assay buffer is added to the assay plate. The assay plate is incubated for 60 minutes at 37° C. Then 5 µl per well of Anti-IP1-Cryptate Tb solution and 5 µl per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

C. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 µL per time point contains TRIS buffer pH 7.6 at room temperature (0.1 M), $MgCl_2$ (5 mM), microsomal protein (1 mg/mL) and the test compound at a final concentration of 1 µM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

D. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_{4\times7}H_2O$, 0.41 mM $NaH_2PO_4 \times H_2O$, 15 mM HEPES, 20 mM glucose, 0.25% BSA, pH 7.4) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Biological Data

Comparison of Assays A and B with the Assays Described in WO03/051872

Comparison of Assays A and B with the Assays Described in WO2013/187466

Assays described in WO2013/187466 differ from assays A and B in:

The technology and readout: fluorescence measurement of intracellular $Ca^{2+}$ changes (WO2013/187466) instead of luminescence measurement of IP1 (assays A and B)

Ox1R and Ox2R overexpressing cell lines used for the assays described in WO2013/187466 are of different origin as cell lines used for assays A and B Use of modified orexin A (2 amino acids substituted) as agonist instead of orexin A Agonist concentration of 300 μM used for the OX1R assay and 3 nM for the OX2R assay (EC75 vs. EC100; according to Okumura T. et al., Biochemical and Biophysical Research Communications, 2001) (WO2013/187466). $IC_{50}$ values that have been reported are dependent on the agonist concentration. Selectivity ratios calculated from these $IC_{50}$ values cannot be compared with the selectivity ratios calculated from the agonist concentration independent Kb values obtained from assay A and B.

Due to these differences between the assays, a direct comparison has to be established. Therefore, examples 69, 70 (the most selective ones) and 5 (one of the most potent ones) described in WO2013/187466 are tested in assays A and B so as to be directly compared with compounds of the present invention (see Table 2a).

TABLE 1

In vitro potencies of compounds of WO03/051872 as reported therein versus as determined in the Assays A, B, C, and D (described above)

| Structure of Example 6 in WO03/051872 | Data as described in WO03/051872 (page 16-18) | | |
|---|---|---|---|
| [chemical structure] | OX1R pKb = 6.4 to 7.4 corresponds to Kb = 400 to 40 nM | OX2R pKb <6.6 to 7.4 corresponds to Kb >250 to 40 nM | OX2RKb/OX1R Kb = not described |

| Data as determined in Assays A and B (0.5 nM Orexin A concentration) | | |
|---|---|---|
| Assay A: OX1R Kb = 30 nM | Assay B: OX2R Kb = 101 nM | OX2RKb/OX1R Kb = 3.4 |

| Data as determined in Assays C and D | |
|---|---|
| Assay C: Human MST t½ = 8 min | Assay D: MDCK efflux ratio (BA/AB) = 0.8 |

TABLE 2a

In vitro potencies of compounds of WO2013/187466 as reported therein versus as determined in the Assays A and B (described above)

| Structure Example # in WO2013/187466 | As described in WO2013/187466 | | | As determined in Assays A and B | | |
|---|---|---|---|---|---|---|
| | OX1R IC$_{50}$ [nM] | OX2R IC$_{50}$ [nM] | OX2R IC$_{50}$/OX1R IC$_{50}$ | OX1R Kb [nM] (Orexin A concentration used) | OX2R Kb [nM] (0.5 nM Orexin A concentration) | OX2R Kb/OX1R Kb |
| [structure 1] | 1.6 | 1896 | 1185 | 2.25 (0.5 nM) | 98 | 43 |
| [structure 2] | 1.1 | 452 | 411 | 1.10 (0.5 nM) 0.72 (50 nM) | 29 | 26 40 |
| [structure 3] | 0.5 | 76 | 152 | 1.78 (0.5 nM) 0.94 (50 nM) | 28 | 16 30 |

Table 2b: Stability in human liver microsomes and MDCK efflux ratios of compounds of WO2013/187466 as determined in the assays C and D (described above)

TABLE 2b

Stability in human liver microsomes and MDCK efflux ratios of compounds of WO2013/187466 as determined in the Assays C and D (described above)

| Example # in WO2013/187466 | Data as determined in Assay C: Human MST $t_{1/2}$ [min] | Data as determined in Assay D: MDCK efflux ratio (BA/AB) |
|---|---|---|
| Example 69 | 23 | 1.3 |
| Example 70 | 16 | 0.8 |
| Example 5 | 30 | 3.1 |

Table 3: In vitro potencies of the structurally closest prior art compounds (Example 91, 84, 90, 40, 73, 46 and 14) in WO2016/034882 as reported therein:

TABLE 3

In vitro potencies of the structurally closest prior art compounds (Example 91, 84, 90, 40, 73, 46 and 14) in WO2016/034882 as reported therein:

| Structure Example # in WO2016/034882 | As described in WO2016/034882 (Table 1, Table 2, Table 3, page 177-180) | | |
|---|---|---|---|
| | OX1R | OX2R | OX2R $IC_{50}$/OX1R $IC_{50}$ |
| (structure 1) | Table 1 and 2: not reported Table 3: $pIC_{50}$ = 7.6 corresponds to $IC_{50}$ = 25 nM | Table 1 and 2: not reported Table 3: $pIC_{50}$ <5.1 corresponds to $IC_{50}$ = 7950 nM | Table 3: 318 |
| (structure 2) | Table 1 and 2: not reported Table 3: $pIC_{50}$ = 8.7 corresponds to $IC_{50}$ = 1.9 nM | Table 1 and 2: not reported Table 3: $pIC_{50}$ = 6.0 corresponds to $IC_{50}$ = 1000 nM | Table 3: 526 |
| (structure 3) | Table 1 and 2: not reported Table 3: $pIC_{50}$ = 8.7 corresponds to $IC_{50}$ = 1.9 nM | Table 1 and 2: not reported Table 3: $pIC_{50}$ = <6.0 corresponds to $IC_{50}$ = 1000 nM | Table 3: >526 |

TABLE 3-continued

In vitro potencies of the structurally closest prior art compounds (Example 91, 84, 90, 40, 73, 46 and 14) in WO2016/034882 as reported therein:

| | As described in WO2016/034882 (Table 1, Table 2, Table 3, page 177-180) | | |
|---|---|---|---|
| Structure Example # in WO2016/034882 | OX1R | OX2R | OX2R $IC_{50}$/OX1R $IC_{50}$ |
| [Structure: 2H-triazole-phenyl with Cl, C(=O)-N(Me)-CH(Et)-CH2-NH-pyrimidine-CF3] | Table 1: $pIC_{50}$ = 7.8 corresponds to $IC_{50}$ = 16 nM Table 2 and 3: not reported | Table 1: $pIC_{50}$ = 5.6 corresponds to $IC_{50}$ = 2500 nM Table 2 and 3: not reported | Table 3: 156 |
| [Structure: 2H-triazole-pyridine with Me, C(=O)-N(Et)-CH(Et)-CH2-NH-pyrimidine-CF3] | Table 1 and 2: not reported Table 3: $pIC_{50}$ = 8.8 corresponds to $IC_{50}$ = 1.6 nM | Table 1 and 2: not reported Table 3: $pIC_{50}$ = <6.0 corresponds to $IC_{50}$ > 1000 nM | Table 3: >625 |
| [Structure: 2H-triazole-pyridine with Me, C(=O)-N(Me)-CH(Et)-CH2-NH-pyrimidine-CF3] | Table 1: $pIC_{50}$ = 7.7 $IC_{50}$ = 20 nM Table 2: $pIC_{50}$ = 7.5 corresponds to $IC_{50}$ = 32 nM Table 3: $pIC_{50}$ = 8.5 corresponds to $IC_{50}$ = 3.2 nM | Table 1: $pIC_{50}$ = 5.1 corresponds to $IC_{50}$ = 7800 nM Table 2: $pIC_{50}$ = <5.0 corresponds to $IC_{50}$ = >10000 nM Table 3: $pIC_{50}$ = <5.0 corresponds to $IC_{50}$ = 10000 nM | Table 1: 390 Table 2: >312 Table 3: 3200 |
| [Structure: biphenyl, C(=O)-N(Me)-CH(Me)-CH2-NH-pyridine-CF3] | Table 1: $pIC_{50}$ = 8.3 corresponds to $IC_{50}$ = 5.0 nM Table 2: $pIC_{50}$ = 7.8 corresponds to $IC_{50}$ = 16 nM Table 3: not reported | Table 1: $pIC_{50}$ = 6.8 corresponds to $IC_{50}$ = 158 nM Table 2: $pIC_{50}$ = 7.2 corresponds to $IC_{50}$ = 63 nM Table 3: not reported | Table 1: 32 Table 2: 4 |

Compounds of the Present Invention

Compounds of the present invention are more potent, more selective and more stable in human liver microsomes than the structurally most similar example, Example 6, disclosed in WO03/051872 (Table 1).

Compounds of the present invention are more selective over OX2R than preferred examples, Examples 5, 69 and 70, disclosed in WO2013/187466. Furthermore, they are more stable in human liver microsomes (Tables 2a and 2b).

A full and detailed comparison of the key biological properties (including OX1R and OX2R potencies, stability in human liver microsomes and MDCK efflux) of all compounds of the present invention with the corresponding closest prior art compounds in WO2016/034882 respectively is shown in Table 4.

Example 7 of the present invention differs structurally from Example 91 in WO2016/034882 i.e. the closest prior art compound in that it contains a central N-ethyl-(propan-2-yl)amino moiety in place of the N-methyl-[butan-2-yl] amino moiety. This structural difference unexpectedly results in Example 7 being 25-fold more potent at OX1R and more selective while being still in an acceptable range with regard to metabolic stability and MDCK efflux.

Examples 1, 2, 3, 4, 5, 6, 8 and 18 are characterized by additional structural features thereby differing structurally farther from Example 91 in WO2016/034882 in that the phenyl group carries a different substituent or has a different substitution pattern. Example 14 has a further structural difference when compared to Example 91 in WO2016/

034882, i.e. a methyl substituted oxadiazole group substitutes for the triazole moiety. Examples 1, 2, 3, 4, 5, 6, 8, 18 and 14 demonstrate a significantly higher potency in conjunction with higher selectivity along with adequate in vitro pharmacokinetic properties.

Examples 11, 13, 15 and 16 of the present invention differ structurally from Example 84 in WO2016/034882, i.e. the closest prior art compound in that they contain a) a central N-ethyl-(propan-2-yl)amino moiety in place of the N-methyl-[butan-2-yl]amino moiety and b) a fluorine-substituted phenyl ring instead of a methyl-substituted pyridyl ring. These structural differences unexpectedly result in Examples 11, 13, 15 and 16 demonstrating an at least 20-fold higher potency and higher selectivity in conjunction with good stability in human liver microsomes and low MDCK efflux.

Example 9 of the present invention differs structurally from Examples 46 and 73 in WO2016/034882, i.e. the closest prior art compound in that they contain a central N-ethyl-(propan-2-yl)amino moiety in place of the N-methyl-[butan-2-yl]amino moiety and N-ethyl-[butan-2-yl]amino moiety, respectively. These structural differences unexpectedly result in Example 9 demonstrating a >10 fold higher potency along with comparable selectivity and adequate pharmacokinetic properties when compared to Example 46 in WO2016/034882. Example 9 is superior to Example 73 in WO2016/034882 as well in that it possesses an approximately 3-fold higher potency and significantly improved stability in human liver microsomes.

Example 10 differs structurally farther from Examples 46 and 73 in WO2016/034882 in that the pyridine nitrogen is positioned differently and that the pyridine moiety is substituted with a fluorine instead of a methyl group. While having comparable potency and acceptable MDCK efflux, Example 10 surprisingly demonstrates higher selectivity and stability in human liver microsomes when compared to Examples 46 and 73 in WO2016/034882.

Example 12 of the present invention differs structurally from Example 90 in WO2016/034882, i.e. the closest prior art compound in that it contains a central N-ethyl-(propan-2-yl)amino moiety in place of the N-methyl-[butan-2-yl] amino moiety. Unexpectedly, Example 12 is superior to Example 90 in WO2016/034882 in that it demonstrates an at least 3 fold higher potency at OX1R with a lower selectivity though enhanced stability in human liver microsomes.

Examples 22, 23 and 24 of the present invention differ structurally from Example 40 in WO2016/034882, the closest prior art compound in that they contain a central N-ethyl-(propan-2-yl)amino moiety in place of the N-methyl-[butan-2-yl]amino moiety. Besides, they possess a differently substituted phenyl group. Furthermore, Example 23 contains a methyl-oxadiazole moiety instead of the triazole one. Examples 22, 23 and 24 are significantly more stable in human liver microsomes and perform within the same potency range or even well beyond when compared to Example 40 in WO2016/034882.

Examples 17, 19, 20 and 21 of the present invention differ structurally from Example 14 in WO2016/034882, i.e. the closest prior art compound in that they contain a central N-ethyl-(propan-2-yl)amino moiety in place of the N-methyl-(propan-2-yl)amino moiety. Furthermore, they include a) a methylpyrimidine, pyridine, pyrimidine or pyrazine moiety instead of a phenyl group and b) a 5-trifluoromethylpyrimidine moiety instead of a 5-chloropyridyl group. Unexpectedly, Examples 17, 19, 20 and 21 are of higher selectivity and markedly higher stability (in human liver microsomes) than Example 14 in WO2016/034882.

These results demonstrate that unexpectedly, compounds of the present invention are superior to the structurally most similar examples disclosed in WO2016/034882 (closest prior art compounds) respectively in at least one of the following key pharmacodynamic and pharmacokinetic parameters including potency, selectivity, stability in human liver microsomes and MDCK efflux.

TABLE 4

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| Ex 91 in WO2016/034882 | 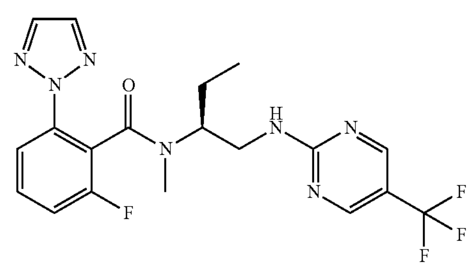 [SMILES: CC[C@@H](CNc1ncc(C(F)(F)F)cn1)N(C)C(=O)c1c(F)cccc1-n1nccn1] | 3.63 (0.5 nM) | 313 | 86 | >120 | <3 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| 7 | 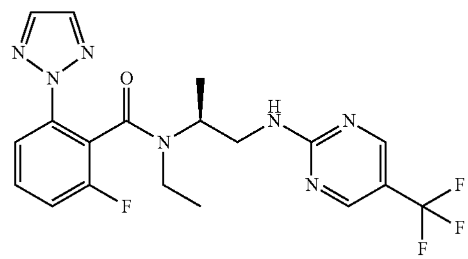 [SMILES: CCN(C(=O)c1c(F)cccc1-n1nccn1)[C@@H](C)CNc1ncc(C(F)(F)F)cn1] | 0.141 (50 nM) | 33.4 | 237 | 76 | <3 |
| 1 | 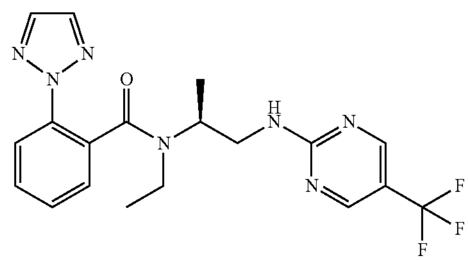 [SMILES: CCN(C(=O)c1ccccc1-n1nccn1)[C@@H](C)CNc1ncc(C(F)(F)F)cn1] | 0.048 (50 nM) | 19.4 | 404 | 120 | <3 |
| 2 | 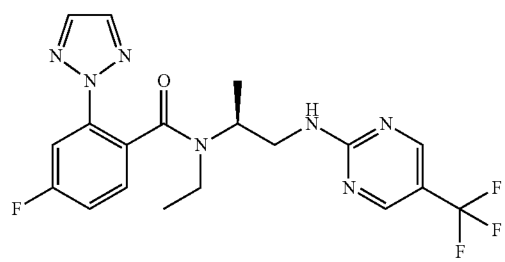 [SMILES: CCN(C(=O)c1ccc(F)cc1-n1nccn1)[C@@H](C)CNc1ncc(C(F)(F)F)cn1] | 0.188 (50 nM) | 64.5 | 343 | 43 | <3 |
| 3 | 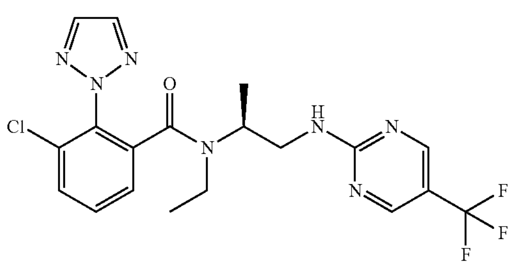 [SMILES: CCN(C(=O)c1cccc(Cl)c1-n1nccn1)[C@@H](C)CNc1ncc(C(F)(F)F)cn1] | 0.015 (50 nM) | 6.27 | 418 | 84 | <3 |
| 4 | 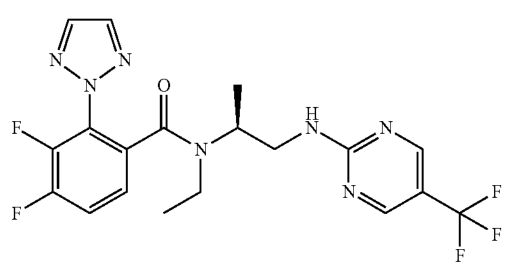 [SMILES: CCN(C(=O)c1ccc(F)c(F)c1-n1nccn1)[C@@H](C)CNc1ncc(C(F)(F)F)cn1] | 0.096 (50 nM) | 46.9 | 489 | 95 | <3 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| 5 | 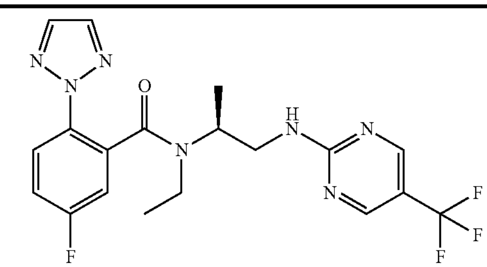 | 0.083 (50 nM) | 35.3 | 425 | 120 | <3 |
| 6 | 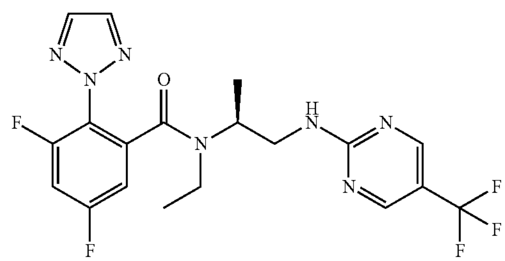 [SMILES: CCN(C(=O)c1cc(F)cc(F)c1-n1nccn1)[C@@H](C)CNc1ncc(C(F)(F)F)cn1] | 0.091 (50 nM) | 53.1 | 584 | >120 | <3 |
| 8 | 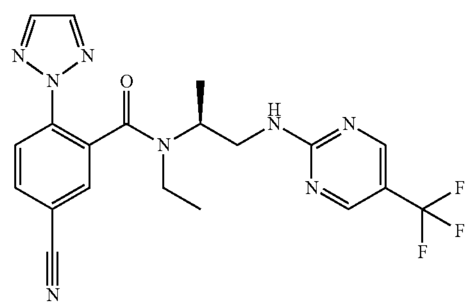 [SMILES: CCN(C(=O)c1cc(C#N)ccc1-n1nccn1)[C@@H](C)CNc1ncc(C(F)(F)F)cn1] | 0.292 (50 nM) | 33.4 | 114 | >120 | 3-5 |
| 18 | 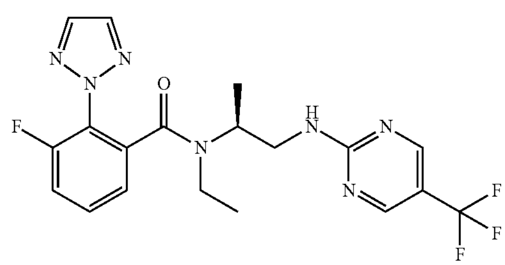 [SMILES: CCN(C(=O)c1cccc(F)c1-n1nccn1)[C@@H](C)CNc1ncc(C(F)(F)F)cn1] | 0.0512 (50 nM) | 18.0 | 352 | >120 | <3 |
| 14 | 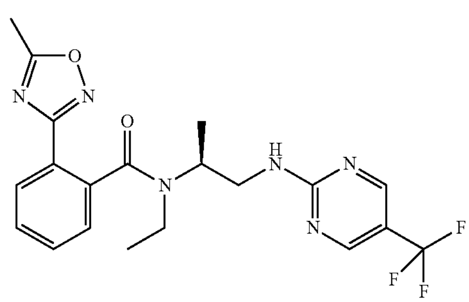 [SMILES: CCN(C(=O)c1ccccc1-c1noc(C)n1)[C@@H](C)CNc1ncc(C(F)(F)F)cn1] | 0.138 (50 nM) | 44.0 | 319 | 91 | <3 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| Ex 84 in WO2016/034882 | 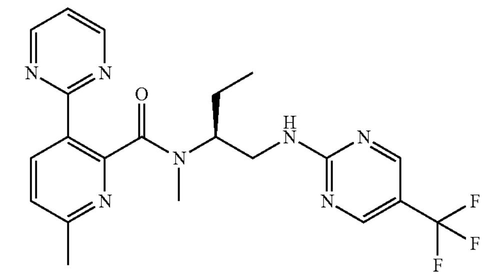 [SMILES: CC[C@@H](CNc1ncc(C(F)(F)F)cn1)N(C)C(=O)c1nc(C)ccc1-c1ncccn1] | 2.20 (0.5 nM) | 229 | 104 | 41 | <3 |
| 11 | 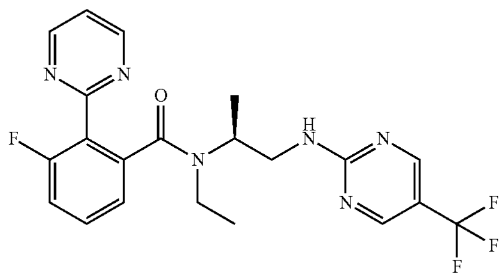 [SMILES: CCN(C(=O)c1cccc(F)c1-c1ncccn1)[C@@H](C)CNc1ncc(C(F)(F)F)cn1] | 0.014 (50 nM) | 19.3 | 1379 | >120 | 3-5 |
| 13 | 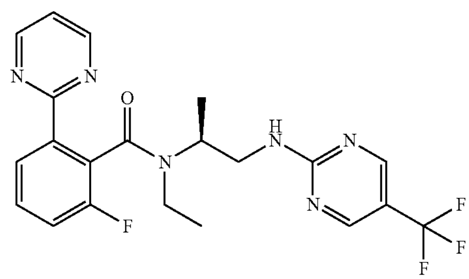 [SMILES: CCN(C(=O)c1c(F)cccc1-c1ncccn1)[C@@H](C)CNc1ncc(C(F)(F)F)cn1] | 0.0925 (50 nM) | 62.0 | 670 | >120 | <3 |
| 15 | 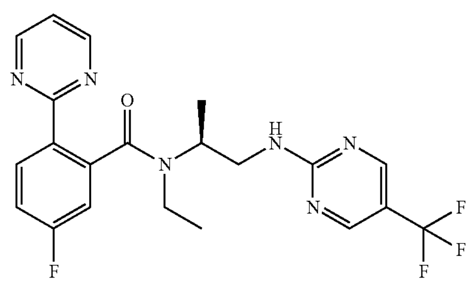 [SMILES: CCN(C(=O)c1cc(F)ccc1-c1ncccn1)[C@@H](C)CNc1ncc(C(F)(F)F)cn1] | 0.0397 (50 nM) | 22.9 | 577 | >120 | <3 |
| 16 | 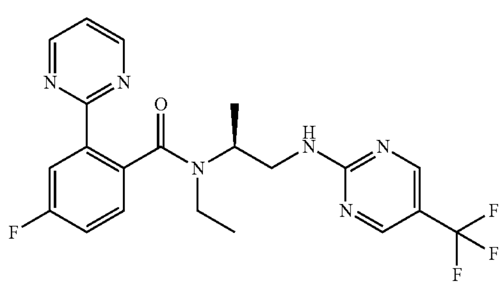 [SMILES: CCN(C(=O)c1ccc(F)cc1-c1ncccn1)[C@@H](C)CNc1ncc(C(F)(F)F)cn1] | 0.0947 (50 nM) | 76.8 | 811 | 100 | <3 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| Ex 90 in WO2016/034882 | 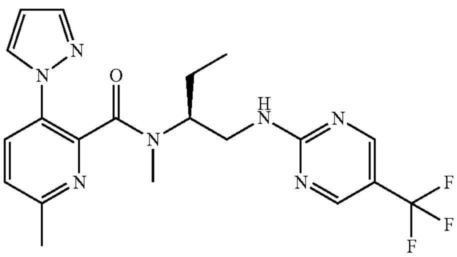 [SMILES: CC[C@@H](CNc1ncc(C(F)(F)F)cn1)N(C)C(=O)c1nc(C)ccc1-n1cccn1] | 1.3 (0.5 nM) 2.3 (50 nM) | 974 | 739 423 | 26 | <3 |
| 12 | 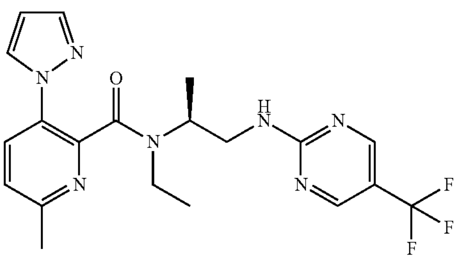 [SMILES: CCN(C(=O)c1nc(C)ccc1-n1cccn1)[C@@H](C)CNc1ncc(C(F)(F)F)cn1] | 0.614 (50 nM) | 129 | 210 | 65 | <3 |
| Ex 40 in WO2016/034882 | 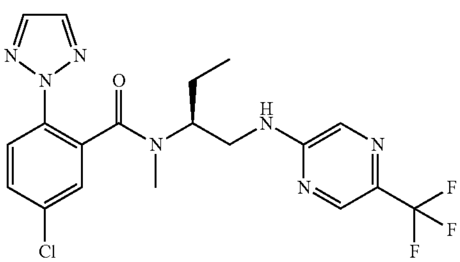 [SMILES: CC[C@@H](CNc1cnc(C(F)(F)F)cn1)N(C)C(=O)c1cc(Cl)ccc1-n1nccn1] | 0.180 (50 nM) | 38 | 211 | 9 | <3 |
| 22 | 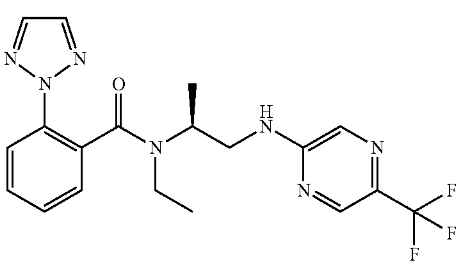 [SMILES: CCN(C(=O)c1ccccc1-n1nccn1)[C@@H](C)CNc1cnc(C(F)(F)F)cn1] | 0.0202 (50 nM) | 7.37 | 366 | >120 | 3-5 |
| 23 | 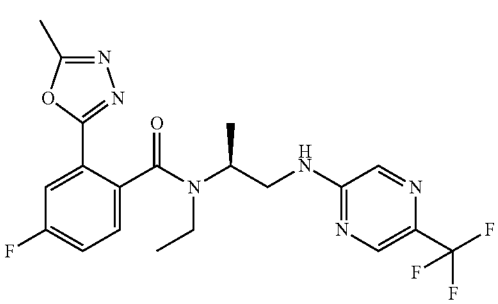 [SMILES: CCN(C(=O)c1ccc(F)cc1-c1nnc(C)o1)[C@@H](C)CNc1cnc(C(F)(F)F)cn1] | 0.558 (50 nM) | 222 | 398 | >120 | 3-5 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| 24 | 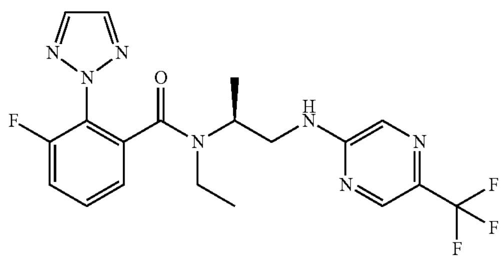 [SMILES: CCN(C(=O)c1cccc(F)c1-n1nccn1)[C@@H](C)CNc1cnc(C(F)(F)F)cn1] | 0.0141 (50 nM) | 10.0 | 709 | 61 | 3-5 |
| Ex 73 in WO2016/034882 | 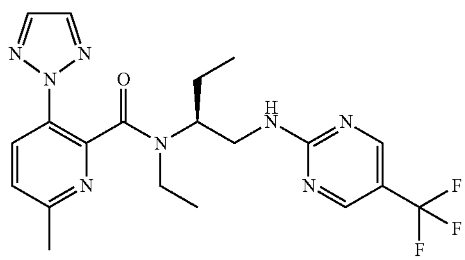 [SMILES: CC[C@@H](CNc1ncc(C(F)(F)F)cn1)N(CC)C(=O)c1nc(C)ccc1-n1nccn1] | 0.309 (50 nM) | 145 | 469 | 11 | <3 |
| Ex 46 in WO2016/034882 | 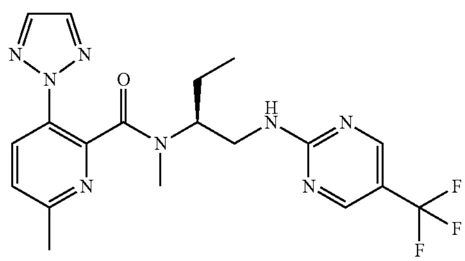 [SMILES: CC[C@@H](CNc1ncc(C(F)(F)F)cn1)N(C)C(=O)c1nc(C)ccc1-n1nccn1] | 1.558 (50 nM) | 372 | 240 | 32 | <3 |
| 9 | 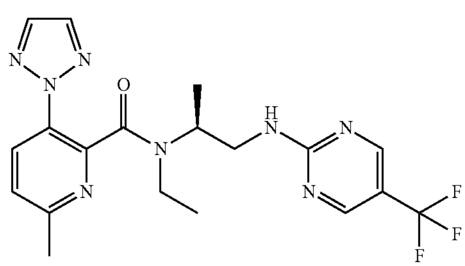 [SMILES: CCN(C(=O)c1nc(C)ccc1-n1nccn1)[C@@H](C)CNc1ncc(C(F)(F)F)cn1] | 0.106 (50 nM) | 32.9 | 310 | 100 | <3 |
| 10 | 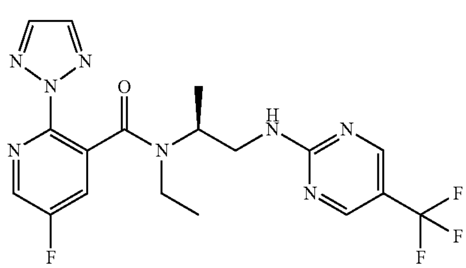 [SMILES: CCN(C(=O)c1cc(F)cnc1-n1nccn1)[C@@H](C)CNc1ncc(C(F)(F)F)cn1] | 1.12 (50 nM) | 1060 | 949 | >120 | <3 |

TABLE 4-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2R Kb/OX1R Kb | Assay C: Human MST t½ [min] | Assay D: MDCK efflux ratio (BA/AB) |
|---|---|---|---|---|---|---|
| Ex 14 in WO2016/034882 | 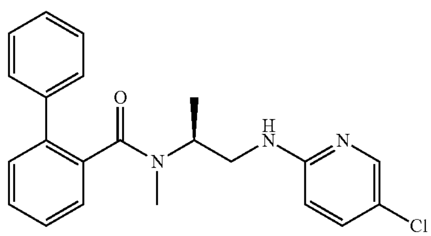 [SMILES: C[C@@H](CNc1ccc(Cl)cn1)N(C)C(=O)c1ccccc1-c1ccccc1] | 0.171 (50 nM) | 4.7 | 27 | 2 | 0.6 |
| 17 | 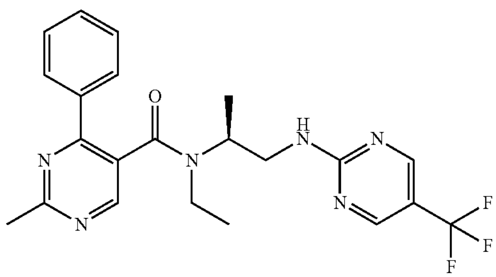 [SMILES: CCN(C(=O)c1cnc(C)nc1-c1ccccc1)[C@@H](C)CNc1ncc(C(F)(F)F)cn1] | 0.0216 (50 nM) | 54.0 | 2500 | >120 | <3 |
| 19 | 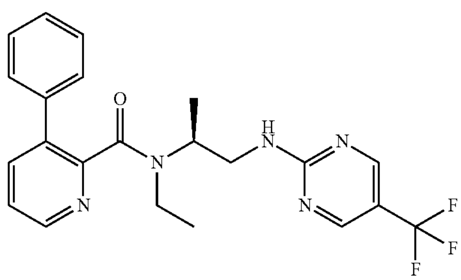 [SMILES: CCN(C(=O)c1ncccc1-c1ccccc1)[C@@H](C)CNc1ncc(C(F)(F)F)cn1] | 0.120 (50 nM) | 12.5 | 104 | >120 | <3 |
| 20 | 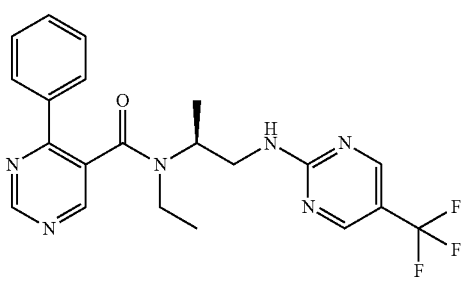 [SMILES: CCN(C(=O)c1cncnc1-c1ccccc1)[C@@H](C)CNc1ncc(C(F)(F)F)cn1] | 0.566 (50 nM) | 68.0 | 120 | 43-100 | <3 |
| 21 | 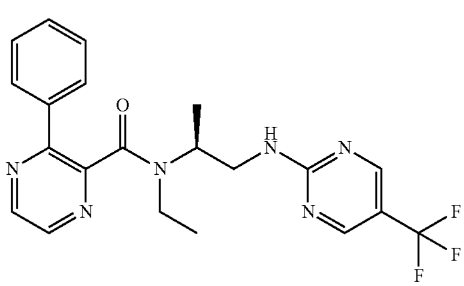 [SMILES: CCN(C(=O)c1nccnc1-c1ccccc1)[C@@H](C)CNc1ncc(C(F)(F)F)cn1] | 0.363 (50 nM) | 55.9 | 154 | >120 | <3 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
- Antidepressants
- Mood stabilizers
- Antipsychotics
- Anxiolytics
- Antiepileptic drugs
- Sleeping agents
- Cognitive enhancer
- Stimulants
- Non-stimulant medication for attention deficit hyperactivity disorder
- Additional psychoactive drugs.

EXPERIMENTAL SECTION

List of Abbreviations

RT room temperature
ESI-MS electrospray ionisation mass spectrometry
APCI atmospheric pressure chemical ionization
aq. aqueous MS mass spectrometry
MeOH methanol
EtOH ethanol
EA ethyl acetate
DMF N,N-dimethylformamide
DCM dichloromethane
DMA dimethylacetamide
TEA triethylamine
THF tetrahydrofuran
dppf 1,1'-bis(diphenylphosphanyl)ferrocene
DIPEA N,N-diisopropylethylamine
HATU 1-[bis(dimethylamino)methylene]-1H-1,2,3-triazolo[4,5-b]pyridinium 3-oxid hexafluorophosphate
DBU 1,8-Diazabicyclo[5.4.0]undec-7-ene
DIAD diisopropyl azodicarboxylate
Rt retention time
h hour(s)
min minutes
sat. saturated
ACN acetonitrile
TFA trifluoroacetic acid
HPLC high-performance liquid chromatography
HPLC-MS high-performance liquid chromatography-mass spectrometry
CIP 2-chloro-4,5-dihydro-1,3-dimethyl-1H-imidazolium hexafluorophosphate HPLC-Methods:

Method Name: A
Column: Venusil XPB-C-18, 2.1×50 mm, 5 μm
Column Supplier: Agela Technologies

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 90 | 10 | 0.8 | 50 |
| 0.40 | 90 | 10 | 0.8 | 50 |
| 3.40 | 0 | 100 | 0.8 | 50 |
| 3.85 | 0 | 100 | 0.8 | 50 |
| 3.86 | 90 | 10 | 0.8 | 50 |
| 4.50 | 90 | 10 | 0.8 | 50 |

Method Name: B
Column: Sunfire C18, 2.1×30 mm, 2.5 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: C
Column: Chromolity Flash RP-18e 25-2 mm
Column Supplier: Merck

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Method Name: D
Column: XBridge BEH Phenyl, 2.1×30 mm, 1.7 μm
Column Supplier: Waters

| Gradient/Solvent Time [min] | % Sol [H$_2$O, 0.1% NH$_3$] | % Sol [Acetonitril] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: E
Column: XBridge C18, 4.6×30 mm, 3.5 μm
Column Supplier: Waters

| Gradient/Solvent Time [min] | % Sol [H2O, 0.1% NH3] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: F
Column: Sunfire C18, 2.1×30 mm, 2.5 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: G
Column: XBridge C18, 3×30 mm, 3.5 μm
Column Supplier: Waters

| Gradient/Solvent Time [min] | % Sol [H2O, 0.1% NH3] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: H
Column: Xselect CSH, 2.5 682 m, 4.6×50 mm/Column Supplier: Waters

| Gradient/Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |

Method Name: I
Column: Xselect CSH Phenyl- Hexyl, 2,5 682 m, 4.6×50 mm
Column Supplier: Waters

| Gradient/Solvent Time [min] | % Sol [90% H₂O +10% ACN + 0.1% HCOOH] | % Sol [90% ACN + 10% H₂O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: J
Column: Sunfire C18, 3.0×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |

Method Name: K
Column: BEH C18, 1.7 682 m, 2.1×50 mm
Column Supplier: Waters

| Gradient/Solvent Time [min] | % Sol [90% H₂O + 10% ACN + 5 nM NH₄HCO₃] | % Sol [90% ACN + 10% H₂O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: L
Column: CSH C18, 1.7 μm, 2.1×50 mm
Column Supplier: Waters

| Gradient/Solvent Time [min] | % Sol [90% H₂O + 10% ACN + 0.1% HCOOH] | % Sol [90% ACN + 10% H₂O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: M
Column: Atlantis T3, 3.0 μm 2.1×50 mm
Column Supplier: Waters

| Gradient/Solvent Time [min] | % Sol [90% H₂O + 10% ACN + 0.1% HCOOH] | % Sol [90% ACN + 10% H₂O] | Flow [mL/min] | Temp [° C.] |
|---|---|---|---|---|
| 0.00 | 100 | 0 | 0.7 | 35 |
| 2.40 | 0 | 100 | 0.7 | 35 |
| 2.70 | 0 | 100 | 0.7 | 35 |
| 2.80 | 100 | 0 | 0.7 | 35 |
| 3.00 | 100 | 0 | 0.7 | 35 |

Method Name: N
Column: Synergi Hydro RP100A, 2.5 μm, 3×50 mm
Column Supplier: Phenomenex

| Gradient/Solvent Time [min] | % Sol [90% H₂O + 10% ACN + 5 mM NH₄COOH] | % Sol [90% ACN + 10% H₂O] | Flow [mL/min] | Temp [° C.] |
|---|---|---|---|---|
| 0.00 | 100 | 0 | 1.2 | RT |
| 4.00 | 0 | 100 | 1.2 | RT |
| 5.30 | 0 | 100 | 1.2 | RT |
| 5.50 | 100 | 0 | 1.2 | RT |
| 6.00 | 100 | 0 | 1.2 | RT |

Method Name: O
Column: HSS C18, 1.8 μm, 2.1×50 mm
Column Supplier: Waters

| Gradient/Solvent Time [min] | % Sol [90% H₂O + 10% ACN + 0.1% CF₃COOH] | % Sol [90% ACN + 10% H₂O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: P
Column: BEH C18, 1.7 μm 2.1×50 mm
Column Supplier: Waters

| Gradient/ Solvent Time [min] | % Sol [90% H₂O + 10% ACN + NH₄COOH 5 mM] | % Sol [90% ACN + 10% H2O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: Q
Column: Venusil XPB-C18, 2.1×50 mm, 5 682 m
Column Supplier: Agilent

| Gradient/Solvent Time [min] | % Sol [H₂O, 0.0375% TFA] | % Sol [ACN, 0.018% TFA] | Flow [mL/min] | Temp [° C.] |
|---|---|---|---|---|
| 0.00 | 90 | 10 | 1.0 | 50 |
| 2.00 | 20 | 80 | 1.0 | 50 |

-continued

| Gradient/Solvent Time [min] | % Sol [H₂O, 0.0375% TFA] | % Sol [ACN, 0.018% TFA] | Flow [mL/min] | Temp [° C.] |
|---|---|---|---|---|
| 2.48 | 20 | 80 | 1.0 | 50 |
| 2.50 | 90 | 10 | 1.0 | 50 |
| 3.00 | 90 | 10 | 1.0 | 50 |

Method Name: R
Column: Luna-C18 5 μm, 2.0*50 mm
Column Supplier: Phenomenes

| Gradient/Solvent Time [min] | % Sol [H₂O, 0.0375% TFA] | % Sol [ACN, 0.018% TFA] | Flow [mL/min] | Temp [° C.] |
|---|---|---|---|---|
| 0.00 | 99 | 1 | 0.8 | 40 |
| 0.40 | 99 | 1 | 0.8 | 40 |
| 3.40 | 0 | 100 | 0.8 | 40 |
| 3.85 | 0 | 100 | 0.8 | 40 |
| 3.86 | 99 | 1 | 0.8 | 40 |
| 4.50 | 99 | 1 | 0.8 | 40 |

Method Name: S
Column: XBridge C18 2.5 μm, 3.0*30 mm
Column Supplier: Waters

| Gradient/Solvent Time [min] | % Sol [Water 0.1% NH3] | % Sol [Acetonitrile] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method Name: T
Column: Atlantis dC18 5 μm 4.6×50 mm
Column Supplier: Waters

| Gradient/Solvent Time [min] | % Sol [90% H₂O + 10% ACN + 0.05% CF₃COOH] | % Sol [90% ACN + 10% H2O] | Flow [mL/min] | Temp [° C.] |
|---|---|---|---|---|
| 0.00 | 100 | 0 | 1.3 | 35 |
| 0.70 | 100 | 0 | 1.3 | 35 |
| 4.50 | 0 | 100 | 1.3 | 35 |
| 5.80 | 0 | 100 | 1.3 | 35 |
| 6.00 | 100 | 0 | 1.3 | 35 |

Method Name: U
Column: Sunfire, 3×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.00 | 0 | 100 | 2.2 | 60 |
| 1.25 | 0 | 100 | 3 | 60 |
| 1.40 | 0 | 100 | 3 | 60 |

HPLC traces and NMR spectra of the examples and some advanced intermediates are of increased complexity due to the fact that these compounds exist in an equilibrium of multiple rotameric forms. In the case of multiple peaks in the HPLC spectrum, the retention time of the main peak is reported.

Preparation of intermediates
Acid intermediates:

| Acid | Name | Structure | Reference/source |
|---|---|---|---|
| A-1 | 2-[1,2,3]Triazol-2-yl-benzoic acid | 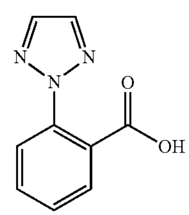 [SMILES: O=C(O)c1ccccc1-n1nccn1] | WO2008/143856, page 30, Compound B-1 |
| A-2 | 3-Fluoro-2-[1,2,3]triazol-2-yl-benzoic acid | 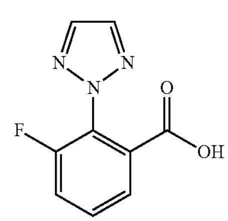 [SMILES: O=C(O)c1cccc(F)c1-n1nccn1] | WO2011/50198, Page 47, Intermediate 5 |

-continued

Preparation of intermediates
Acid intermediates:

| Acid | Name | Structure | Reference/source |
|---|---|---|---|
| A-3 | 4-Fluoro-2-[1,2,3]triazol-2-yl-benzoic acid | 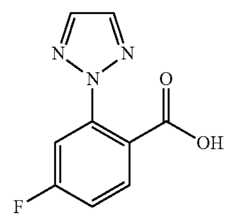 [SMILES: O=C(O)c1ccc(F)cc1-n1nccn1] | WO2011/50200, Page 54, Intermediate 16 |
| A-4 | 3-Chloro-2-[1,2,3]triazol-2-yl-benzoic acid | 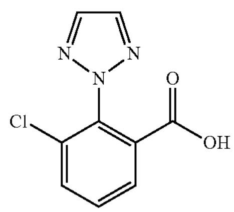 [SMILES: O=C(O)c1cccc(Cl)c1-n1nccn1] | WO2013/68935 E-23 in Table 6, p. 57 |
| A-5 | 5-Fluoro-2-[1,2,3]triazol-2-yl-benzoic acid | 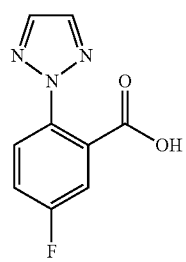 [SMILES: O=C(O)c1cc(F)ccc1-n1nccn1] | WO2011/50198, Page 45-46, Intermediate 1 |
| A-6 | 5-Cyano-2-[1,2,3]triazol-2-yl-benzoic acid | 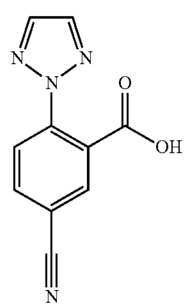 [SMILES: N#Cc1ccc(-n2nccn2)c(C(=O)O)c1] | WO2012/85852, Page 50, Intermediate 39 |
| A-7 | 4-Fluoro-2-pyrimidin-2-yl-benzoic acid | 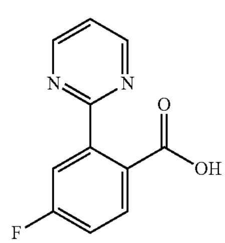 [SMILES: O=C(O)c1ccc(F)cc1-c1ncccn1] | WO2011/50200, page 95, intermediate 85 |
| A-8 | 2-Fluoro-6-[1,2,3]triazol-2-yl-benzoic acid | 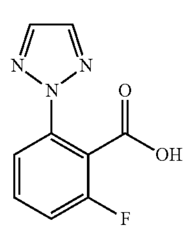 [SMILES: O=C(O)c1c(F)cccc1-n1nccn1] | WO2012/145581, intermediate 12, page 49-50 |

-continued

Preparation of intermediates
Acid intermediates:

| Acid | Name | Structure | Reference/source |
|---|---|---|---|
| A-9 | 3-Fluoro-2-pyrimidin-2-yl-benzoic acid | 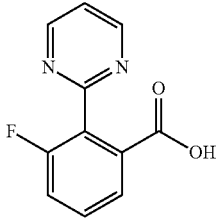 [SMILES: O=C(O)c1cccc(F)c1-c1ncccn1] | WO2011/50200, page 78, Intermediate 52 |
| A-10 | 5-Fluoro-2-pyrimidin-2-yl-benzoic acid | 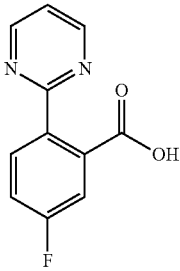 [SMILES: O=C(O)c1cc(F)ccc1-c1ncccn1] | WO2011/50200, page 54-57, Intermediate 17 |
| A-11 | 2-Fluoro-6-pyrimidin-2-yl-benzoic acid | 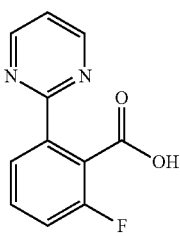 [SMILES: O=C(O)c1c(F)cccc1-c1ncccn1] | WO2011/50198 A1, page 52, Intermediate 14 |
| A-12 | 6-Methyl-3-[1,2,3]triazol-2-yl-pyridine-2-carboxylic acid | 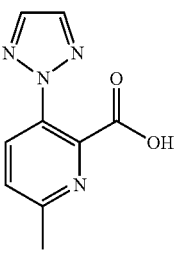 | WO2012/89606, Page 44, Intermediate D40 |
| A-13 | 6-Methyl-3-pyrazol-1-yl-pyridine-2-carboxylic acid | 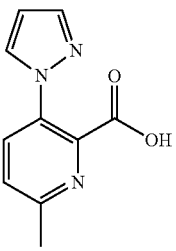 | WO2010/122151, Page 47, Intermediate D37 |
| A-14 | 2-Methyl-4-phenyl-pyrimidine-5-carboxylic acid | 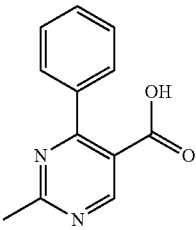 [SMILES: Cc1ncc(C(=O)O)c(-c2ccccc2)n1] | commercially available from Fluorochem catalog number 322095, MDL number: MFCD02682072 |

Preparation of intermediates
Acid intermediates:

| Acid | Name | Structure | Reference/source |
|---|---|---|---|
| A-15 | 3-Phenyl-pyridine-2-carboxylic acid | 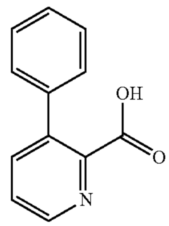 [SMILES: O=C(O)c1ncccc1-c1ccccc1] | commercially available from Fluorochem catalog number 065974, MDL number: MFCD04114112 |
| A-16 | 4-Phenyl-pyrimidine-5-carboxylic acid | 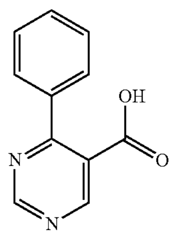 [SMILES: O=C(O)c1cncnc1-c1ccccc1] | commercially available from Emolecules catalog number 45773153, MDL number: MFCD09835877 |
| A-17 | 3-Phenyl-pyrazine-2-carboxylic acid | 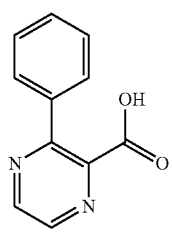 [SMILES: O=C(O)c1nccnc1-c1ccccc1] | commercially available from Fluorochem catalog number 079153, MDL number: MFCD02181157 |

3,5-Difluoro-2-[1,2,3]triazol-2-yl-benzoic acid A-18:

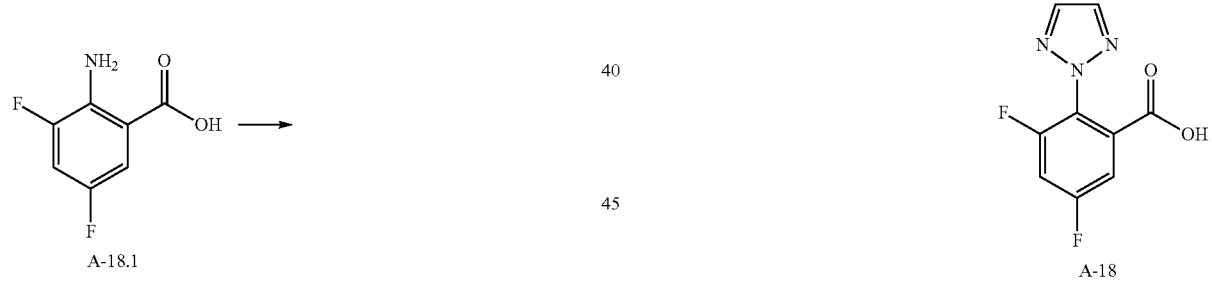

Step 1: A mixture of A-18.1 (9.80 g, 0.55 mmol) in water (70 mL) and H$_2$SO$_4$ (25.0 mL, 0.48 mol) is cooled to 0° C. Then NaNO$_2$ (4.8 g, 69 mmol) in H$_2$O (20 mL) is added dropwise and the reaction mixture is stirred for 1.5 h. To this mixture KI (45.0 g, 0.27 mol) in H$_2$O (40 mL) is added slowly. The reaction mixture is warmed to RT and then heated to 90° C. for 90 min. The mixture is allowed to cool to RT and Na$_2$S2O$_3$ (aq. solution) is added until the color disappears. The precipitate is filtered and then taken up in NaOH (4M aq. solution). The mixture is filtered, the filtrate is acidified with HCl (4M aq. solution) and the precipitate is filtered off, washed with water and dried to give 9.0 g of A-18.2. ESI-MS: 285 [M+H]$^+$; HPLC (Rt): 0.71 min (method C) Step 2: A mixture of A-45.2, (3.50 g, 11.1 mmol), A-18.3 (1.56 g, 22.2 mmol), CuI (0.18 g, 0.89 mmol), A-18.4 (0.70 mL, 4.44 mmol) and K$_2$CO$_3$ (3.46 g, 23.9 mmol) in DMF (10 mL) is heated to 100° C. by microwave for 1.5 h. The mixture is poured into water and extracted with EA. The organic phase is washed with water. The combined aqueous phases are acidified with HCl (0.5M aq. solution) and extracted with EA. The organic phase is washed with brine, dried and concentrated to give the crude product which is purified by HPLC-MS (using a solvent gradient H₂O+0.075% TFA with 5-35% ACN) to provide 1.3 g of A-18. ESI-MS: 226 [M+H]⁺; HPLC (Rt): 1.88 min (method A)

4-Fluoro-2-(5-methyl-[1,3,4]oxadiazol-2-yl)-benzoic acid A-19:

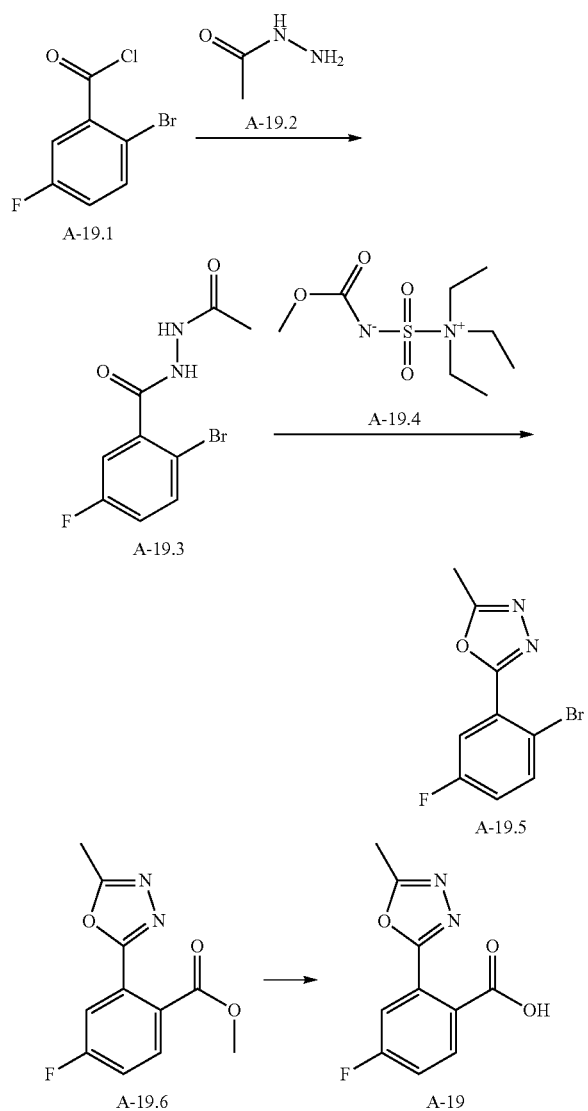

Step 1: To a mixture of A-19.1 (2.00 g, 8.42 mmol) in dry DCM (50 mL) is added A-19.2 (0.83 g, 10.1 mmol) and stirred at RT for 1 h. Another portion of A-19.2 (0.83 g, 10.1 mmol) is added and the reaction is stirred overnight. MeOH (5.0 mL) is added and the solvent is reduced to half the volume. The precipitate is filtered to provide 0.5 g of A-19.3. The filtrate is concentrated and purified by flash column chromatography on silica gel (using a solvent gradient from 100% DCM to 95% DCM and 5% MeOH) to provide another 1.10 g of A-19.3. ESI-MS: 275 [M+H]⁺; HPLC (Rt): 0.11 min (method D)

Step 2: To a mixture of A-19.3 (1.57 g, 5.71 mmol) in DCM (50 mL) is added A-19.4 (2.70 g, 11.3 mmol) and the mixture is stirred overnight. Na₂CO₃ (2 M aq. solution) is added, the organic phase is extracted with Na₂CO₃ (2 M aq. solution), the combined organic phases are washed with brine, dried and concentrated to provide 0.80 g of A-19.5. ESI-MS: 257.3 [M+H]⁺; HPLC (Rt): 0.47 min (method D)

Step 3: To a mixture of A-19.5 (0.80 g, 3.10 mmol), dry MeOH (10 mL) and TEA (1.08 mL, 7.46 mmol) is added Pd(dppf)Cl₂.DCM (152 mg, 0.19 mmol). The reaction is stirred at 70° C. under a pressure of carbon monoxide (3 bar) for 4 h. The mixture is filtered, concentrated and purified by HPLC-MS (using a solvent gradient H₂O/ACN with NH₄OH) to provide 0.55 g of A-19.6. ESI-MS: 237.1 [M+H]⁺; HPLC (Rt): 0.88 min (method E)

Step 4: A mixture of A-19.6 (0.55 g, 2.31 mmol), MeOH (4.0 mL) and NaOH (4M aq. solution, 2.88 mL, 11.5 mmol) is stirred at RT for 30 min. The mixture is concentrated and acidified with HCl (4M aq. solution) to pH2 and extracted with EA, the organic phase is dried and concentrated to provide 0.40 g of A-19. ESI-MS: 223.4 [M+H]⁺; HPLC (Rt): 0.10 min (method D)

3,4-Difluoro-2-[1,2,3]triazol-2-yl-benzoic acid A-20

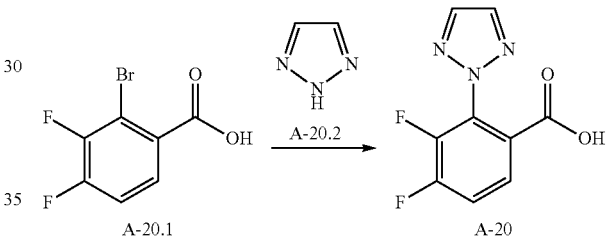

A mixture of A-20.1 (9.00 g, 36.1 mmol), A-20.2 (5.25 g, 72.1 mmol), CuI (0.70 g, 3.61 mmol) and K₂CO₃ (11.3 g, 77.6 mmol) in DMF (100 mL) is heated to 120° C. for 16 h. The mixture is acidified with HCl (0.5M aq. solution) to pH2. The mixture is extracted with EA, the organic phase is washed with brine, dried and concentrated to give the crude product which is purified by prep. HPLC-MS (using a solvent gradient H₂O+0.075% TFA with 5-35% ACN) to provide 3.00 g of A-20. ESI-MS: 248 [M+Na]⁺; HPLC (Rt): 0.45 min (method B)

5-Fluoro-2-[1,2,3]triazol-2-yl-nicotinic acid A-21:

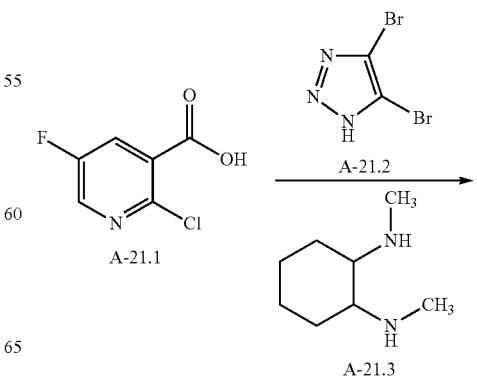

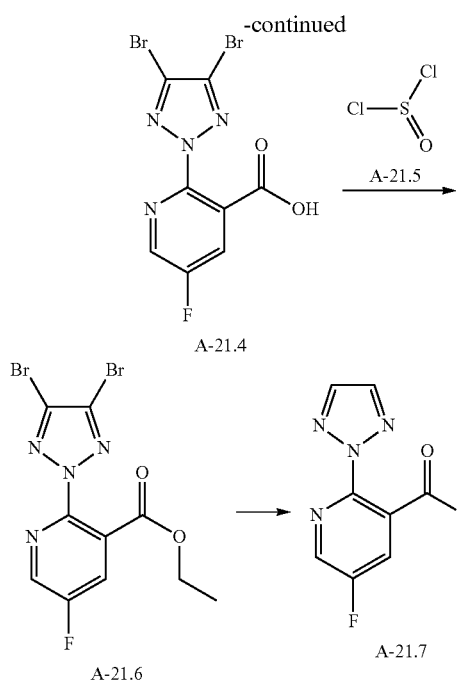

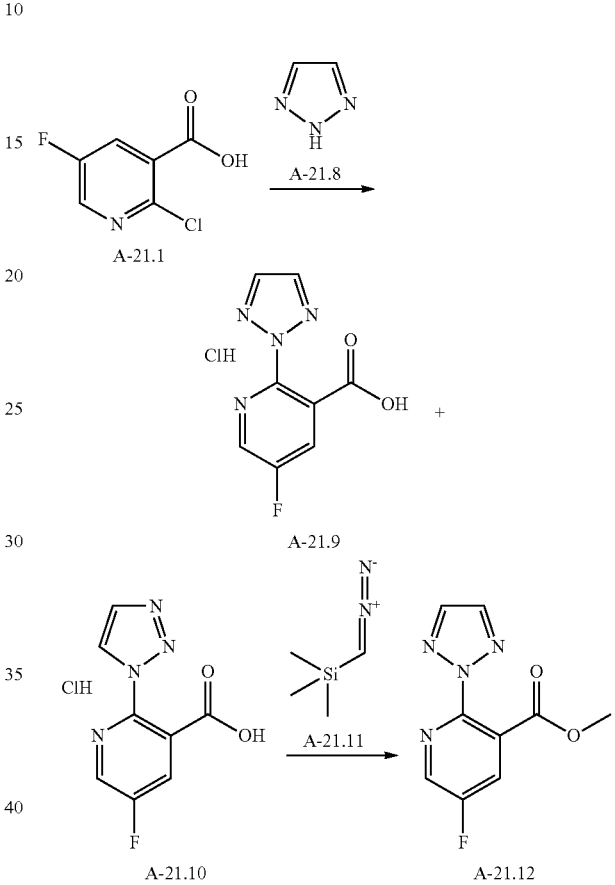

Step 4: To a mixture of A-21.7 (0.85 g, 2.52 mmol) in water (5.0 mL) and THF (15 mL) is added LiOH monohydrate (0.32 g, 7.60 mmol) and the mixture is stirred at RT overnight. The mixture is concentrated and the water phase is acidified with HCl (4M aq. solution) and extracted with DCM. The organic phase is dried and concentrated to afford 0.6 g of A-21. ES+/−: 209 [M+H]$^+$; HPLC (Rt): 0.61 min (method O).

Alternative route for A-21:

Step 1: A mixture of A-21.1 (2.00 g, 11.0 mmol), A-21.2 (3.88 g, 17.1 mmol), CuI (0.13 g, 0.68 mmol), A-21.3 (0.15 mL, 1.03 mmol) and K$_2$CO$_3$ (2.36 g, 17.1 mmol) in dry DMF (10 mL) is heated to 120° C. by microwave for 40 min. The mixture is poured into water and extracted with Et$_2$O. The aq. phase is acidified with HCl (4M aq. solution) and extracted with EA. The combined organic phases are dried and concentrated to give the crude product which is purified by flash column chromatography on silica gel (using a solvent gradient from 100% EA to EA/MeOH=9/1) to provide 3.6 g of A-21.4. APCI+/−: 365 [M+H]$^+$; HPLC (Rt): 1.10 min (method N).

Step 2: To A-21.4 (3.60 g, 7.87 mmol) in anhydrous EtOH (36 mL) is added dropwise A-21.5 (0.86 mL, 11.8 mmol). The mixture is heated to reflux overnight, then concentrated. The crude product is purified by flash column chromatography on silica gel. The so-obtained compound is taken up into DCM and washed with NaHCO$_3$ (sat. solution). The organic phase is dried and concentrated to provide 2.30 g of A-21.6. ES+/−: 395 [M+H]$^+$; HPLC (Rt): 1.23 min (method P).

Step 3: To A-21.6 (2.0 g, 5.0 mmol) dissolved in EtOH (25 mL) is added TEA (1.4 mL, 10 mmol) and palladium on carbon (10%, 0.20 g, 1.88 mmol). The reaction is stirred overnight under an atmosphere of hydrogen (2 bar). The mixture is filtered through a Celite pad and the concentrated. The residue is dissolved in DCM and washed with citric acid (sat. aq. solution). The organic phase is dried and concentrated to afford 1.4 g of A-21.7. ES+/−: 237 [M+H]$^+$; HPLC (Rt): 0.88 min (method P).

Step 1: A mixture of A-21.1 (15.0 g, 81.0 mmol), A-21.8 (11.0 g, 0.16 mol), CuI (0.94 g, 4.90 mmol) and Cs$_2$CO$_3$ (53.0 g, 0.16 mol) in 1,4-dioxane (60 mL) and H$_2$O (0.50 mL) is heated to 100° C. by microwave for 10 min. The mixture is poured into water and extracted with EA. The organic phase is washed with water and aq. phase is acidified with HCl (5M aq. solution) and extracted with EA. The combined organic phases are washed with brine, dried and concentrated to afford 12 g of a mixture of A-21.9 and A-21.10.

Step 2: The mixture of A-21.9 and A-21.10 (4.0 g, 6.5 mmol) is dissolved in MeOH (50 mL) and A-21.11 is added dropwise to the mixture cooled to 0° C. The reaction is stirred at RT overnight. The mixture is quenched with acetic acid and the product is extracted with EA. The organic phase is washed with water and brine, dried and concentrated. The crude product is purified by preparative HPLC (using a solvent gradient H$_2$O/CAN with NH$_4$HCO$_3$) to afford 2.6 g of A-21.12 as a single isomer. ESI-MS: 223 [M+H]$^+$; HPLC (Rt): 0.77 min (method P). The hydrolysis of A-21.12 is carried out in analogy to the conversion of A-21.7 to A-21.

2-(5-Methyl-[1,2,4]oxadiazol-3-yl)-benzoic acid A-22

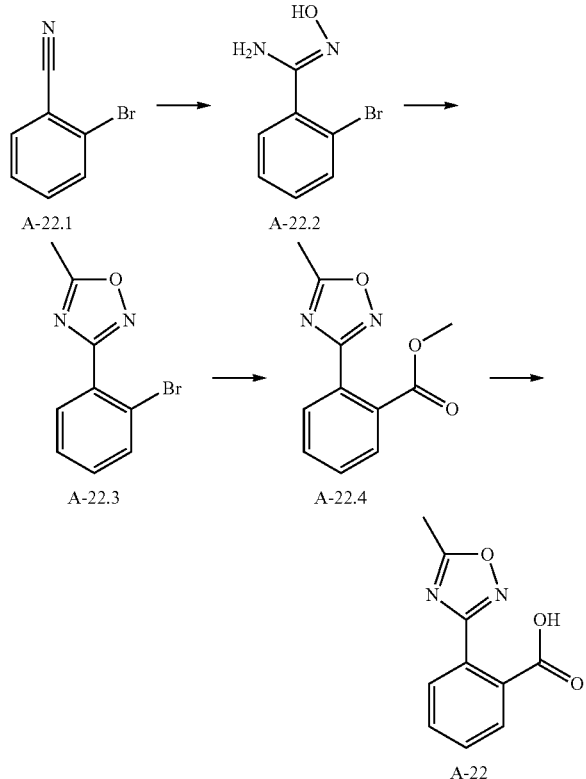

C. for 30 min. A-22.1 (30.0 g, 0.17 mol) is added and the reaction mixture is heated to 70° C. for 12 h. After filtration, the mixture is concentrated and the residue is purified by flash column chromatography on silica gel (using petroleum ether/EA=5:1 to 2:1) to obtain 25 g of A-22.2.

Step 2: To a mixture of A-22.2 (18.0 g, 0.08 mol) in ACN (200 mL) is added acetic anhydride (10.3 g, 0.10 mol) and TEA (16.9 g, 0.17 mol). The mixture is stirred at 120° C. for 48 h. The mixture is concentrated under vacuum and the residue is purified by flash column chromatography on silica gel (using petroleum ether/EA=1/0 to 10/1) to afford 9.0 g of A-22.3. ESI-MS: 239/241 [M+H]$^+$; HPLC (Rt): 1.43 min (method Q)

Step 3: To a mixture of A-22.3 (9.00 g, 0.04 mol) and TEA (11.5 g, 0.11 mol) in MeOH (200 mL) Pd(dppf)Cl$_2$.DCM (1.00 g, 1.20 mmol) is added. The mixture is stirred at 50° C. under an atmosphere of carbon monoxide (50 psi) for 16 h. The mixture is concentrated and the residue is purified by flash column chromatography on silica gel (using petroleum ether/EA=1/0 to 5/1) to afford 4.0 g of A-22.4. ESI-MS: 219 [M+H]$^+$; HPLC (Rt): 1.28 min (method Q)

Step 4: To a mixture of A-22.4 (4.00 g, 0.02 mol) in MeOH (40 mL) and H$_2$O (4.0 mL) is added NaOH (1.47 g, 0.04 mol) at 25° C. under a nitrogen atmosphere. The mixture is stirred at 70° C. for 4 h and is then concentrated. The residue is taken up in H$_2$O, acidified with HCl (4M aq. solution) to pH3 and the precipitate is filtered to provide 2.2 g of A-22 as an HCl salt. ESI-MS: 205 [M+H]$^+$; HPLC (Rt): 2.13 min (method R)

Synthesis of Amine Intermediates

Step 1: A mixture of NH$_2$OH—HCl (28.6 g, 0.41 mol) and K$_2$CO$_3$ (56.9 g, 0.41 mol) in EtOH (500 mL) is stirred at 25°

N-[(2S)-2-(ethylamino)propyl]-5-(trifluoromethyl)pyrimidin-2-amine hydrochloride B-1:

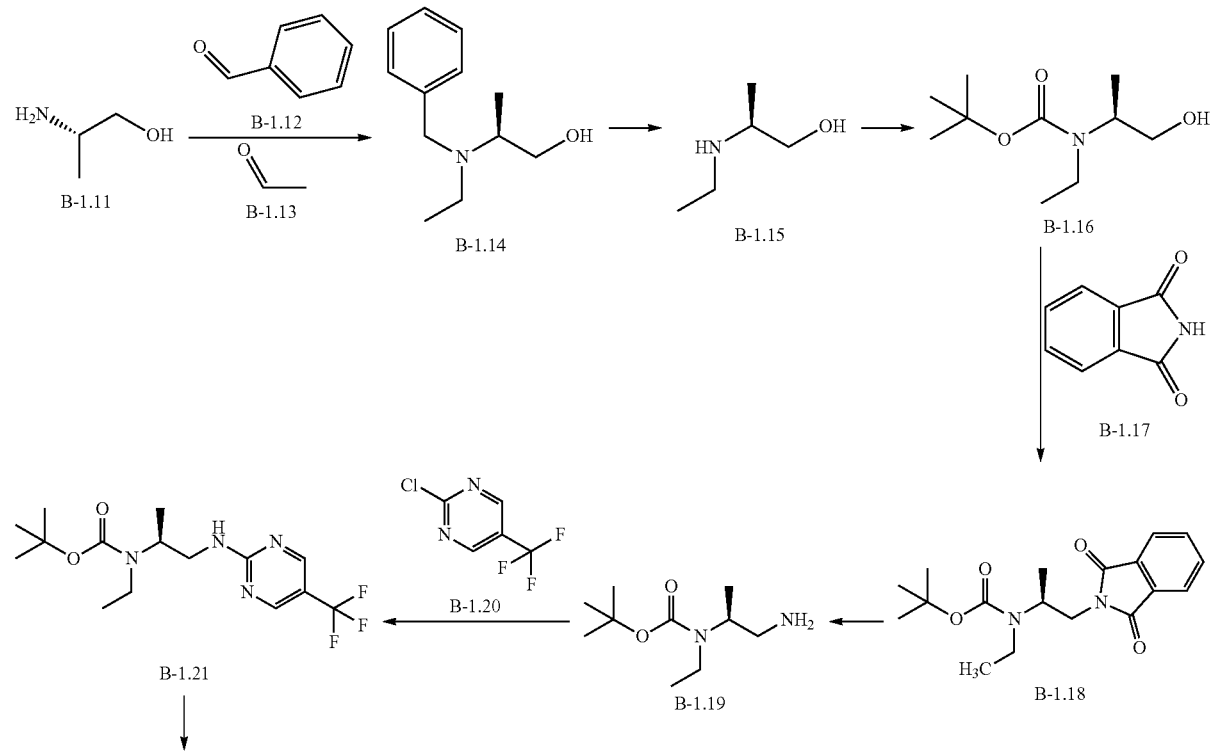

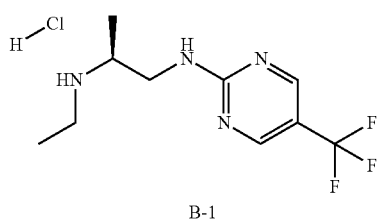

B-1

Step 1: A mixture of B-1.11 (5.0 g, 66 mmol), B-1.12 (6.8 mL, 66 mmol) in anhydrous THF (180 mL) is stirred at RT for 1 h. Sodium triacetoxyborohydride (44.6 g, 0.20 mol) is added at 0° C. and the mixture is stirred at RT for 30 min. B-1.13 (11.0 mL, 0.20 mol) in THF (20 mL) is added dropwise within 10 min at 0° C. and the mixture is stirred at RT overnight. Additional B-1.13 (10 mL) is added and stirred at RT for 3 h. The precipitate is filtrated and washed with THF and DCM. NaHCO$_3$ (sat. aq. solution, 200 mL) and solid NaHCO$_3$ are added until gas formation is terminated. The water phase is extracted with DCM, dried and concentrated to provide 12 g of B-1.14. ESI-MS: 194 [M+H]$^+$; HPLC (Rt): 1.13 min (method E).

Step 2: To a mixture of B-1.14 (3.47 g, 18.0 mmol) in MeOH (4.9 mL) is added Pd/C (350 mg). The mixture is stirred at RT for 16 h under an atmosphere of hydrogen (3 bar). The mixture is filtered through a celite pad and the solvent is evaporated to afford 2.7 g of B-1.15. ESI-MS: 130 [M+H]$^+$; HPLC (Rt): 0.27 min (method P).

Step 3: B-1.15 (3.15 g, 22.6 mmol) and di-tert-butyldicarbonate (5.42 g, 24.8 mmol) are dissolved in THF (100 mL). Under stirring DIPEA (10.0 mL, 58.4 mmol) is added portionwise and the mixture is stirred at RT for 3 h. The mixture is concentrated and the residue is dissolved in DCM. The mixture is washed with H$_2$O, NaOH (1N aq. solution), HCl (1N aq. solution) and NaCl (sat. aq. solution). The organic phase is dried and concentrated. The crude product is purified by flash column chromatography on silica gel (using a solvent gradient from 100% cyclohexane to 60% cyclohexane and 40% EA) to afford 4.5 g of B-1.16. ESI-MS: 204 [M+H]$^+$; HPLC (Rt): 0.92 min (method P).

Step 4: To a mixture of B-1.16 (4.50 g, 22.1 mmol), B-1.17 (5.00 g, 34.0 mmol) and PPh$_3$ (8.90 g, 33.9 mmol) in dry THF (80 mL) is added DIAD (6.00 mL, 33.2 mmol) dropwise at 0° C. and under a nitrogen atmosphere. The mixture is stirred at RT for 16 h. The solvent is concentrated, the residue is treated with H$_2$O and extracted with EA. The organic layer is separated, dried and concentrated. The residue is purified by flash column chromatography on silica gel (using a solvent mixture of n-hexane/EA/MeOH 70/30/1) to get 4.4 g of B-1.18. ESI-MS: 333 [M+H]$^+$; HPLC (Rt): 1.25 min (method P).

Step 5: MeNH$_2$ (33% in EtOH, 20 mL) is added to B-1.18 (1.20 g, 3.61 mmol) at RT. The mixture is stirred for 20 h. Then cooled in ice-water and the solid is filtered and washed with cold EtOH. The solvent is evaporated and the residue is treated with cold citric acid (10% aq. solution). The mixture is extracted with EA. The organic layer is separated. The water phase is treated with NH$_4$OH and extracted with EA. The organic layer is separated, dried and concentrated to afford 650 mg of B-1.19. ESI-MS: 203 [M+H]$^+$; HPLC (Rt): 0.65 min (method P).

Step 6: To a stirred mixture of B-1.19 (1.88 g, 9.29 mmol) and DIPEA (2.50 mL, 14.6 mmol) in NMP (20 mL) is added at RT under a nitrogen atmosphere B-1.20 (2.20 g, 12.1 mmol). The mixture is stirred in microwave at 100° C. for 30 min. The mixture is poured into H$_2$O and extracted with EA. The organic phase is separated, washed with citric acid (10% aq. solution) and H$_2$O. The organic layer is dried and concentrated. The residue is purified by flash column chromatography on silica gel (using a solvent mixture of n-hexane/EA 80/20) to get 2.7 g of B-1.21. ESI-MS: 349 [M+H]$^+$; HPLC (Rt): 1.34 min (method P).

Step 7: HCl (4 M in dioxane, 40 mL) is added to a stirred mixture of B-1.21 (5.50 g, 15.8 mmol) in dioxane (10 mL) at RT and the mixture is stirred for 2 h. The solvent is evaporated. The residue is treated with EA and the solid is filtered to afford 3.5 g of B-1. ESI-MS: 249 [M+H]$^+$; HPLC (Rt): 0.63 min (method P).

N[(2S)-2-(Ethylamino)propyl]-5-(trifluoromethyl)pyrazin-2-amine hydrochloride B-2:

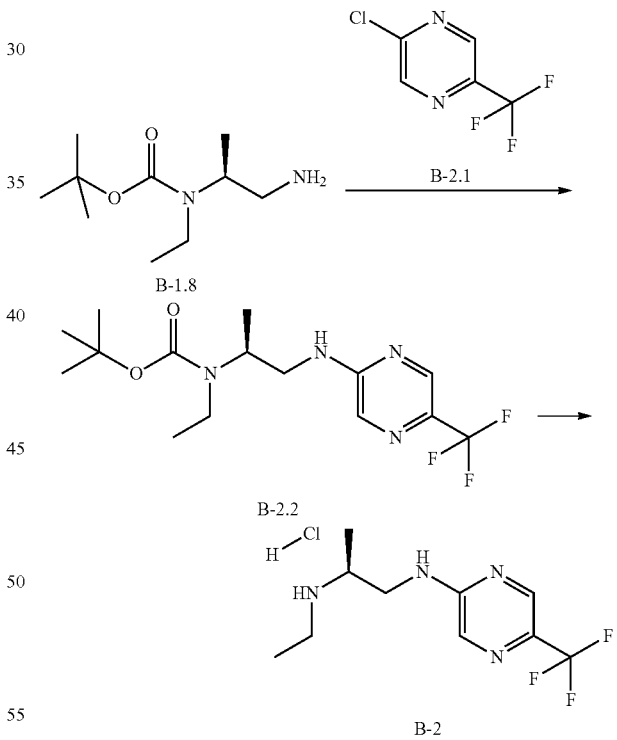

Step 1: To a stirred mixture of B-1.8 (1.00 g, 4.90 mmol) and DIPEA (1.4 mL, 8.0 mmol) in NMP (8.0 mL) is added at RT under a nitrogen atmosphere B-1.9 (0.8 mL, 6.4 mmol). The reaction is heated at 100° C. in microwave for 30 min. The reaction is poured into water and extracted with EA. The organic layer is separated, washed with citric acid (10% aq. solution) and water. The organic layer is dried and concentrated. The residue is purified by flash column chromatography on silica gel (using CH/EA 80/20 as eluent). After evaporation 1.0 g of B-1.10 is obtained. ES+/−: 349 [M+H]$^+$; HPLC (Rt): 1.36 min (method P).

Step 2: HCl (4M in dioxane, 20 mL) is added to a mixture of B-1.10 (1.50 g, 4.30 mmol) in dioxane (5.0 mL) at 0° C. then it is stirred at RT overnight. The solvent is removed and the residue is treated with Et₂O to afford 830 mg of B-1. ES+/−: 249 [M+H]⁺; HPLC (Rt): 0.67 min (method P).

terf-Butyl N-[(2S)-2-(ethylamino)propyl]carbamaie hydrochloride b-3

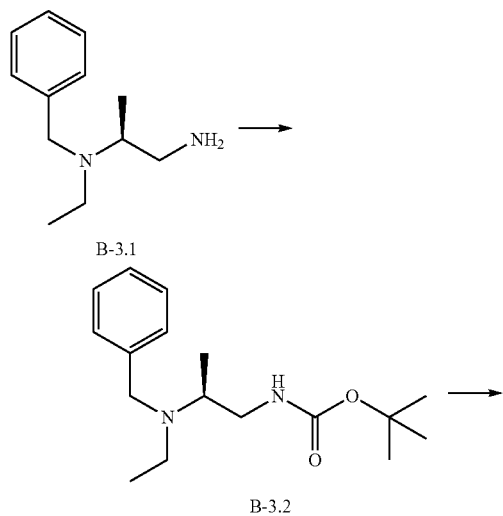

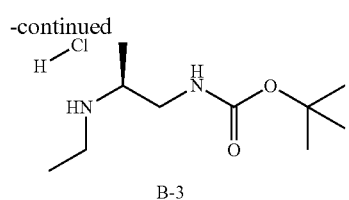

Step 1: Di-tert-butyldicarbonate (1.50 g, 6.87 mmol) in THE (10 mL) is added dropwise to a stirred mixture of B-3.1 (1.32 g, 6.86 mmol) in THF (20 mL) at RT. After 16 h the solvent is evaporated and the residue is purified by flash column chromatography on silica gel (using a solvent mixture of n-hexane/EA/MeOH 80/20/1) to afford 1.7 g of B-3.2. ES+/−: 293 [M+H]+; HPLC (Rt): 1.31 min (method P).

Step 2: B-3.2 (900 mg, 3.08 mmol) is dissolved in MeOH (50 mL). Pd/C (120 mg, 0.11 mmol) is added and the mixture is stirred under an atmosphere of hydrogen (3 bar) overnight. The mixture is filtered through celite and the solution is concentrated to afford 500 mg of B-3. ES+/−: 203 [M+H]+; HPLC (Rt): 0.58 min (method P).

N-[(2S)-1-aminopropan-2-yl]-N-ethyl-3-fluoro-2-(pyrimidin-2-yl)benzamide C-1:

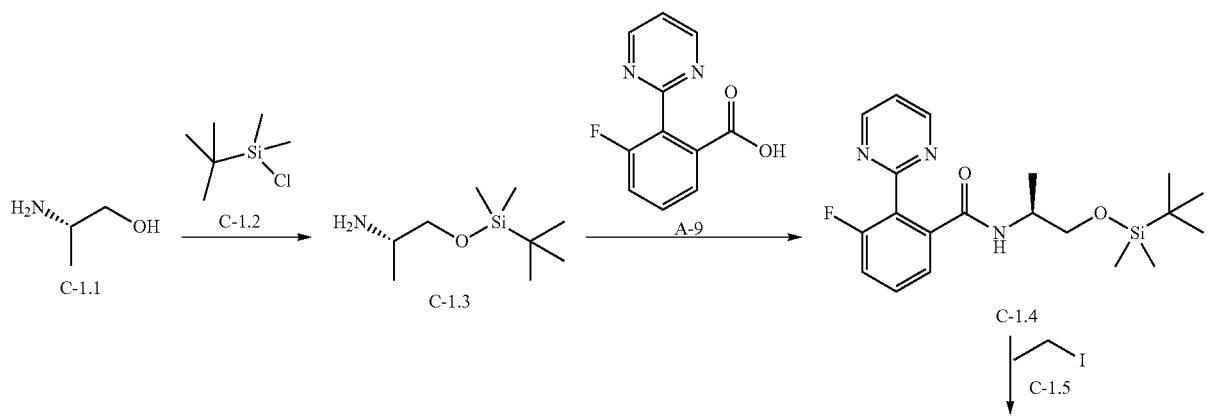

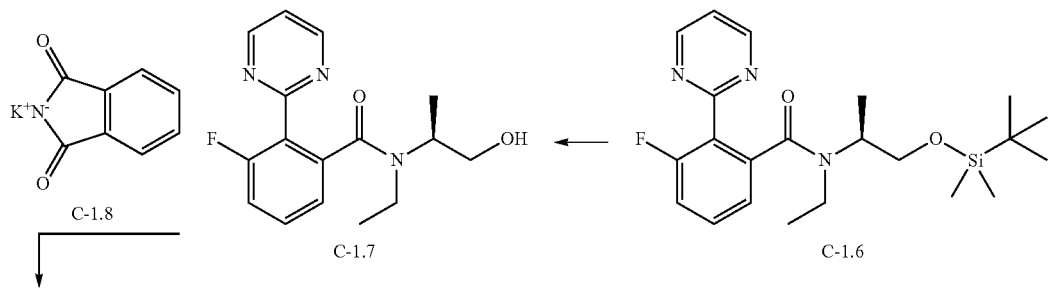

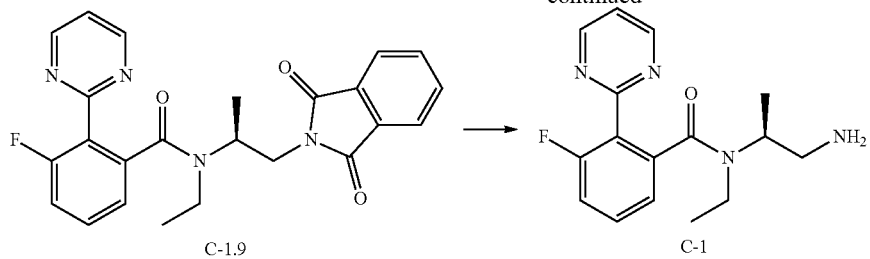

Step 1: A mixture of C-1.2 (10 g, 67 mmol) in DCM (30 mL) is added dropwise to a stirred mixture of C-1.1 (5.0 g, 67 mmol) and TEA (19.0 mL, 0.13 mol) in DCM (70 mL). The mixture is stirred at RT overnight, then a NH$_4$Cl (sat. aq. solution) is added and the aqueous phase extracted with DCM. The organic phase is dried and concentrated to afford 10 g of C-1.3. ESI-MS: 189 [M+H]$^+$; HPLC (Rt): 0.84 min (method P).

Step 2: To a mixture of A-9 (2.49 g, 11.4 mmol) in dry DMF (40 mL) under a nitrogen atmosphere is added DIPEA (5.8 mL, 34 mmol) and HATU (5.7 g, 15 mmol) and the mixture is stirred for 10 min. C-1.3 (2.4 g, 13 mmol) is added and the mixture is stirred at RT for 16 h. The mixture is treated with water and the aqueous phase extracted with EA. The organic phase is separated, washed with NaHCO$_3$ (sat. aq. solution) and citric acid (5% aq. solution), dried and concentrated. The residue is purified by flash column chromatography on silica gel (using n-hexane/EA 50/50) to obtain 2.7 g of C-1.4. ESI-MS: 389 [M+H]$^+$; HPLC (Rt): 1.30 min (method P).

Step 3: NaH (330 mg, 60% suspension in mineral oil, 8.24 mmol) is added to a stirred mixture of C-1.4 (2.14 g, 5.49 mmol) and C-1.5 (883 µL, 11.0 mmol) in dry DMF (3 mL) at 0° C. under a nitrogen atmosphere. The mixture is stirred at 0° C. for 2 h. Water is added and the aqueous phase extracted with Et$_2$O. The organic layer is dried and concentrated to afford 2.3 g of C-1.6. ESI-MS: 418 [M+H]$^+$; HPLC (Rt): 1.50 min (method P).

Step 4: TBAF (765 mg, 0.86 mL, 0.86 mmol) is added to a stirred mixture of C-1.6 (200 mg, 0.43 mmol) in THF (5.0 mL) under stirring at 0° C. The mixture is stirred at 0° C. for 30 min, concentrated and the residue purified by flash column chromatography on silica gel (using a solvent gradient from 100% DCM to 97% DCM/3% MeOH) to afford 130 mg of C-1.7. ESI-MS: 304 [M+H]$^+$; HPLC (Rt): 0.68 min (method P).

Step 5: Methanesulfonylchloride (30.0 aL, 0.39 mmol) is added to a stirred mixture of C-1.7 (100 mg, 0.33 mmol) and DIPEA (70.0 aL, 0.41 mmol) in dry DCM at −10° C. After 2 h the reaction is treated with water. The organic phase is separated, dried and concentrated under reduced pressure without heating. To the residue is added C-1.8 (70.0 mg, 0.38 mmol) and DMF at RT under stirring. After 1 h the reaction is poured into water and extracted with EA. The organic layer is separated, dried and concentrated. The residue is purified by flash column chromatography on silica gel (using n-hexane/EA/MeOH 50/50/1) to afford 75 mg of C-1.9. ESI-MS: 433 [M+H]$^+$; HPLC (Rt): 3.71 min (method N).

Step 6: N$_2$H$_4$×H$_2$O (30.0 µL, 0.60 mmol) is added to a mixture of C-1.9 (60.0 mg, 0.14 mmol) in EtOH (3.0 mL) at RT. The mixture is stirred for 20 h. The mixture is poured into ice-water and the solid is filtered washing with cold EtOH. The solvent is evaporated and the residue is treated with cold citric acid (10% aq. solution). The mixture is extracted with EA. The organic phase is separated, the water phase is treated with NH$_4$OH and extracted with EA. Organic layer is separated, dried and concentrated to get 30 mg of C-1. ES+/−: 303 [M+H]$^+$; HPLC (Rt): 0.58 min (method P).

Alternative route to C-1 from C-1.7

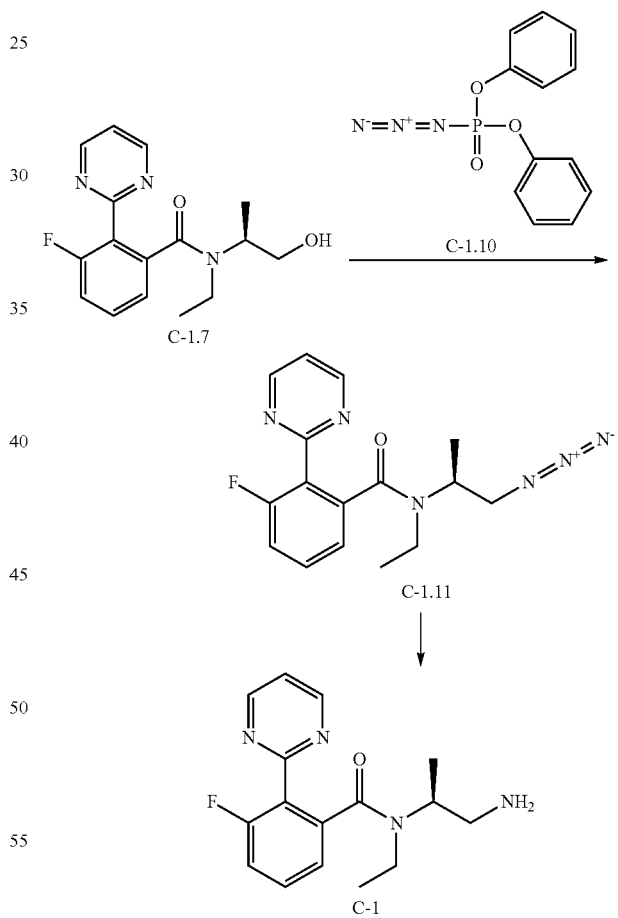

Step 1: To a stirred mixture of C-1.7 (100 mg, 0.33 mmol) and DBU (100 µL, 0.67 mmol) in dry THF (4.0 mL) at RT under a nitrogen atmosphere is added C-1.10 (90.0 µL, 0.42 mmol). After 16 h the mixture is concentrated and the residue is purified by flash column chromatography on silica gel (using n-hexane/EA/MeOH 80/20/1) to afford 80 mg of C-1-11. ESI-MS: 329 [M+H]$^+$; HPLC (Rt): 0.94 min (method P).

Step 2: PPh₃ (160 mg, 0.61 mmol) is added to a stirred mixture of C-1.11 (80.0 mg, 0.24 mmol) in THF (5.0 mL) and water (0.24 mL) at RT under a nitrogen atmosphere. After 16 h the mixture is concentrated and the residue is treated with HCl (1M aq. solution) and the aqueous phase is washed with EA. The aqueous phase is treated with NH₄OH (aq. solution) until pH 10-11 and extracted with DCM. The organic layer is separated, dried and concentrated to afford 65 mg of C-1. ES+/−: 303 [M+H]⁺; HPLC (Rt): 0.58 min (method P).

N-[(2S)-1-aminopropan-2-yl]-N-ethyl-3-fluoro-2-(2H-1,2,3-triazol-2-yl)benzamide C-2:

The residue is purified by prep. HPLC (using a solvent gradient H₂O/ACN with NH₄OH) and combined with the dried solid to provide 3.4 g of C-2.4. ESI pos.+neg. (Loop-Inj.) [M+H]: 422; HPLC (Rt): 0.97 min (method G).

Step 5: To a mixture of C-2.4 (3.4 g, 8.0 mmol) in EtOH (100 mL) is added at RT N₂H₄×H₂O (1.2 mL, 20 mmol) and the reaction is stirred overnight. Another portion of N₂H₄× H₂O (0.50 mL) is added and the reaction is stirred at 60° C. for 2 h. The solid is filtered. The solvent is evaporated and the residue is dissolved in EA and extracted with HCl (1M aq. solution). The acidic aqueous layer is washed with EA, then the pH is adjusted with NH₄OH (25% aq. solution) to

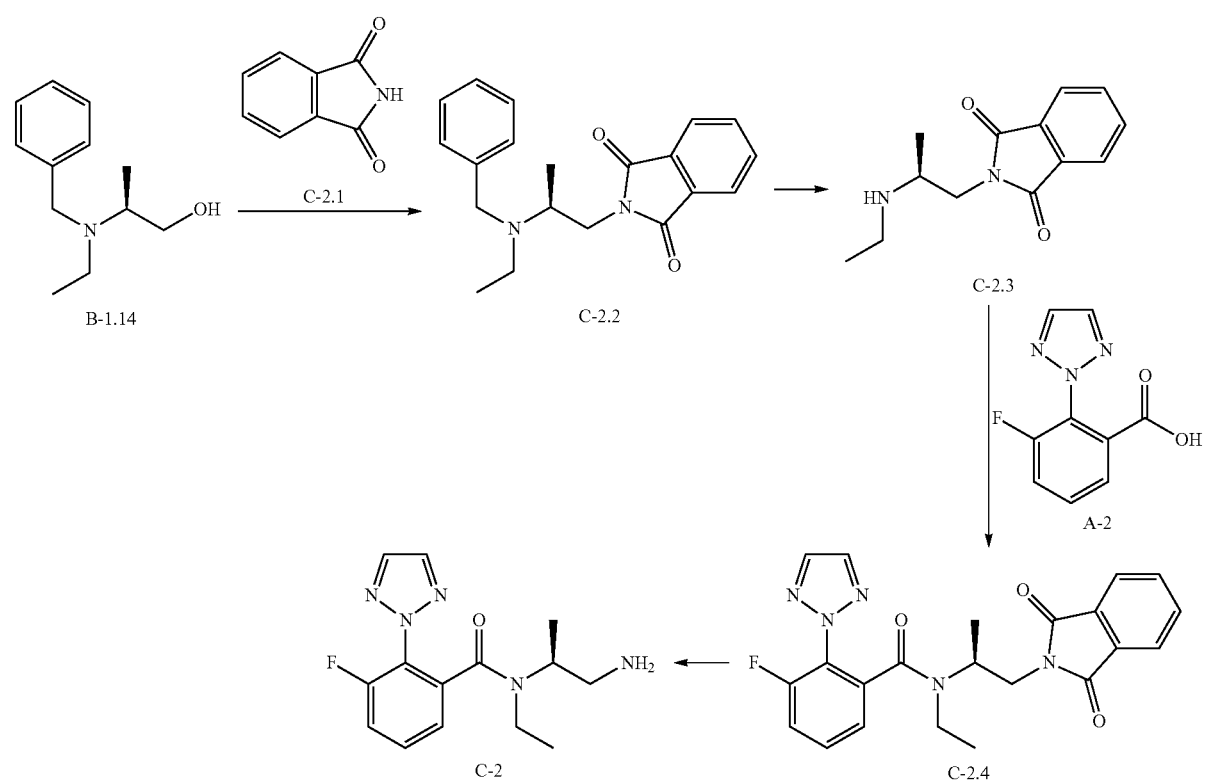

Step 1: To a mixture of B-1.14 (10.0 g, 0.05 mol) and C-2.1 (7.60 g, 0.05 mol) in THF (150 mL) is added PPh₃ (13.6 g, 0.05 mol). Then DIAD (8.80 g, 0.05 mol) is added dropwise at 0° C. The mixture is stirred at RT for 12 h. The reaction mixture is concentrated and the residue is purified by flash column chromatography on silica gel (using petroleum ether/EA from 20/1 to 10/1) to afford 10 g of C-2.2.

Step 2: To a mixture of C-2.2 (2.00 g, 0.01 mol) in MeOH (30 mL) is added Pd/C (1.0 g). The mixture is stirred at 20° C. for 12 h under an atmosphere of hydrogen (50 psi). The mixture is filtered and the filtrate is concentrated to afford 800 mg of C-2.3.

Step 3: To a mixture of C-2.3 (2.50 g, 9.30 mmol) in dry ACN (50 mL) is added A-2 (2.30 g, 11.0 mmol), DIPEA (4.8 mL, 28 mmol) and CIP (3.1 g, 11 mmol) and the mixture is stirred at RT for 2 h. Another portion of A-2 (200 mg) and CIP (500 mg) are added and the reaction is stirred for another 2 h. Then another portion of DIPEA (1.5 mL) and CIP (300 mg) are added and the reaction is stirred for 2 h. Water (70 mL) is added to the reaction mixture is stirred for 1 h. The precipitate is filtered and dried. The mother liquid is extracted with EA, dried and concentrated.

pH=10. The aqueous phase is extracted with EA, dried and concentrated to afford 2.1 g of C-2. ESI pos.+neg. (Loop-Inj.) [M+H]: 292 [M+H]⁺; HPLC (Rt): 0.70 min (method U).

Amides

N-Ethyl-2-fluoro-6-iodo-N-[(S)-1-methyl-2-(5-trifluoromethyl-pyridin-2-yloxy)-ethyl]-Benzamide D-1

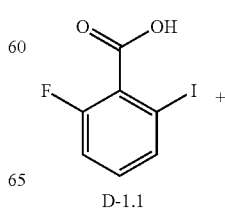

D-1.1 +

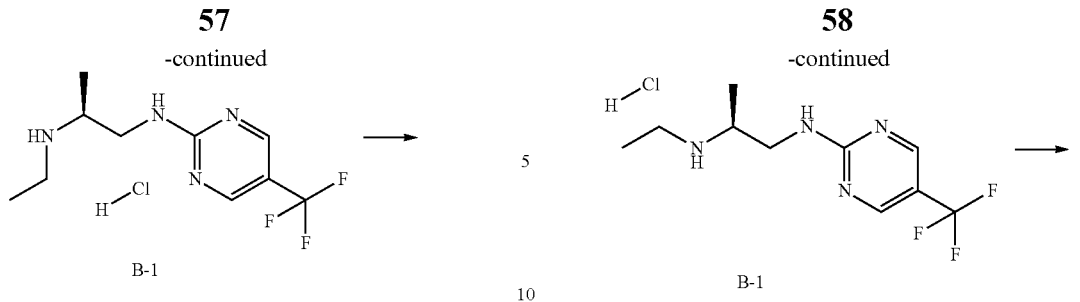

D-1.1 (150 mg, 0.56 mmol) is dissolved in dry DCM (3.0 mL). Under stirring oxalylchloride (846 mg, 1.13 mmol) and a drop of DMF are added and the mixture is stirred for 2 h. The mixture is concentrated and the residue is taken up with dry DCM (3.0 mL). The resulting mixture is added dropwise to a mixture of B-1 (145 mg, 0.51 mmol) and DIPEA (390 µL, 2.30 mmol) in DCM (4.0 mL) at 0° C. The cold bath is removed and the mixture is stirred for 2 h. The crude product is diluted with DCM and washed with NH$_4$Cl (sat. solution), KHCO$_3$ (sat. solution) and water. The organic phase is dried and concentrated. The residue is purified by flash column chromatography (using a solvent gradient from 100% Cyclohexane to Cyclohexane/EA 65/35) to afford 160 mg of compound D-1. ESI-MS: 497 [M+H]$^+$; HPLC (Rt): 1.21 min (Method P).

Preparation of Compounds of the Present Invention

Example 1

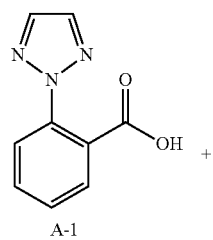

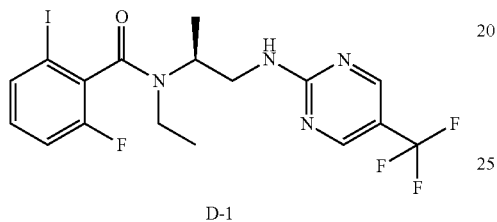

CIP (76 mg, 0.27 mmol) is added to a stirred mixture of A-1 (48 mg, 0.25 mmol), B-1 (60 mg, 0.21 mmol) and DIPEA (109 µL, 0.63 mmol) in dry ACN (2.0 mL) at RT. After 16 h the reaction is treated with ACN/water and purified by preparative LCMS (using a solvent gradient H$_2$O/ACN with NH$_4$OH) to afford 50 mg of compound Example 1. ESI-MS: 420 [M+Na]$^+$; HPLC (Rt): 1.02 min (method G).

The following examples are prepared in analogy to the above described procedure using the corresponding acid (see Acid Intermediates) and amine (see Amine Intermediates) as described before. For Example 4 the workup and purification is adapted: The crude is concentrated and the residue is taken up in EA and washed with citric acid (10% aq. solution), Na$_2$CO$_3$ (aq. sat. solution) and water, dried and concentrated. The residue is purified by flash column chromatography on silica gel (using cyclohexane to cyclohexane/EA 4/6).

For some examples the reaction times are adapted: 4 h for Example 7; 1 h for Example 9; 2 h at 60° C. for Example 16:

| Example | Structure | ESI-MS [M + H]+ | HPLC (Rt) [min] | HPLC Method |
|---|---|---|---|---|
| 2 | 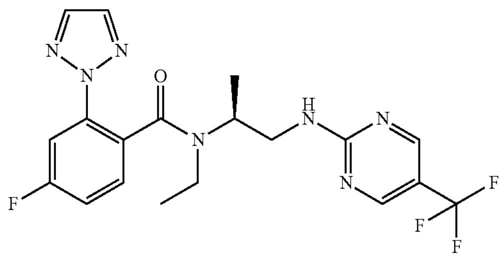 [SMILES: CCN(C(=O)c1ccc(F)cc1-n1nccn1)[C@@H](C)CNc1ncc(C(F)(F)F)cn1] | 438 | 0.83 | S |
| 4 | 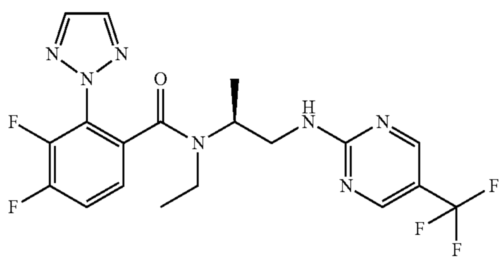 [SMILES: CCN(C(=O)c1ccc(F)c(F)c1-n1nccn1)[C@@H](C)CNc1ncc(C(F)(F)F)cn1] | 456 | 3.19 | H |
| 5 | 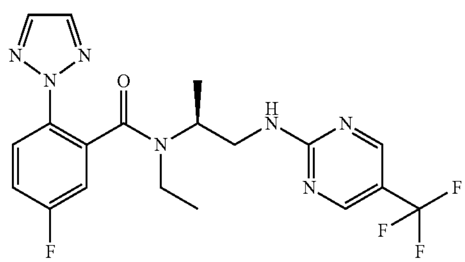 [SMILES: CCN(C(=O)c1cc(F)ccc1-n1nccn1)[C@@H](C)CNc1ncc(C(F)(F)F)cn1] | 438 | 1.02 | G |
| 8 | 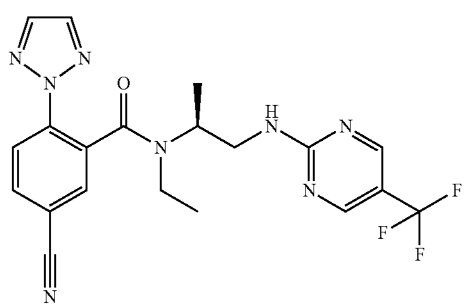 [SMILES: CCN(C(=O)c1cc(C#N)ccc1-n1nccn1)[C@@H](C)CNc1ncc(C(F)(F)F)cn1] | 445 | 0.77 | S |
| 9 | 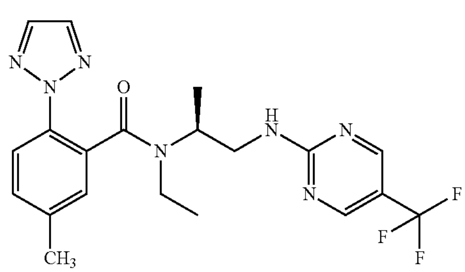 [SMILES: CCN(C(=O)c1cc(C)ccc1-n1nccn1)[C@@H](C)CNc1ncc(C(F)(F)F)cn1] | 435 | 1.04 | G |

| Example | Structure | ESI pos. + neg. (Loop-Inj.) [M + H]+ | HPLC (Rt) | HPLC Method |
|---|---|---|---|---|
| 10 | 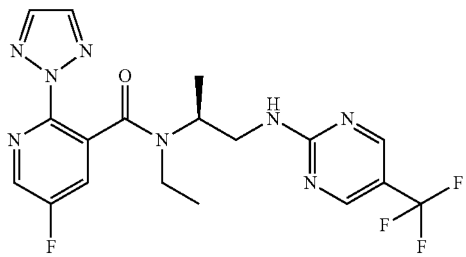 [SMILES: CCN(C(=O)c1cc(F)cnc1-n1nccn1)[C@@H](C)CNc1ncc(C(F)(F)F)cn1] | 439 | 0.71 | S |
| 12 | 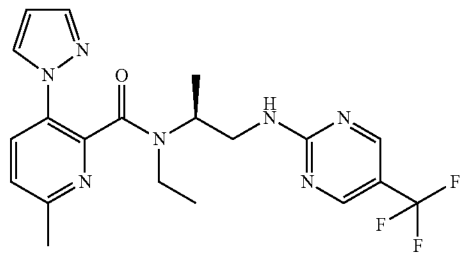 [SMILES: CCN(C(=O)c1nc(C)ccc1-n1cccn1)[C@@H](C)CNc1ncc(C(F)(F)F)cn1] | 434 | 0.81 | S |
| 20 | 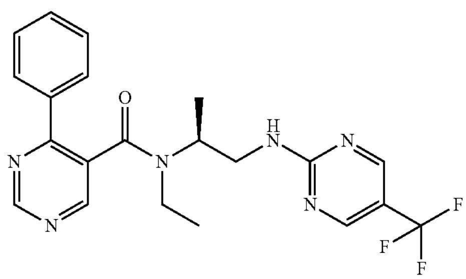 [SMILES: CCN(C(=O)c1cncnc1-c1ccccc1)[C@@H](C)CNc1ncc(C(F)(F)F)cn1] | 431 | 0.79 | S |
| 21 | 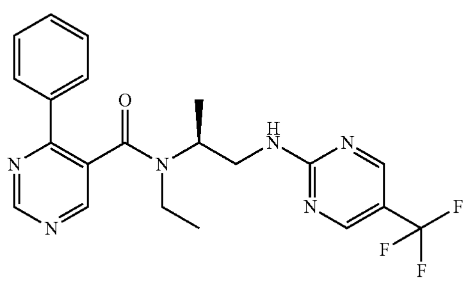 [SMILES: CCN(C(=O)c1cncnc1-c1ccccc1)[C@@H](C)CNc1ncc(C(F)(F)F)cn1] | 431 | 1.02 | G |
| 7 | | 438 | 1.07 | G |

| 16 | 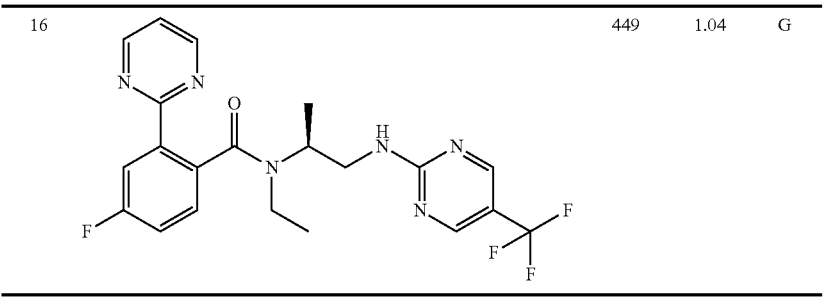 | 449 | 1.04 | G |

Example 3

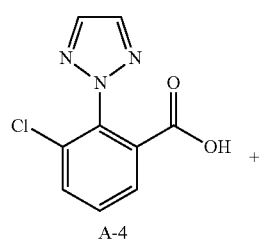
A-4

+

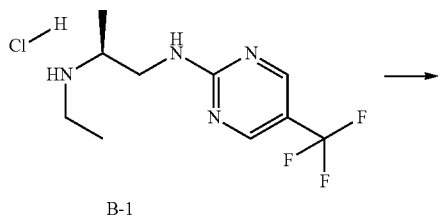
B-1

→

-continued

[Structure of Example 3]

Example 3

A-4 (61 mg, 0.27 mmol) is dissolved in dry DMF (2 mL). HATU (112 mg, 0.30 mmol) and DIPEA (127 μL, 0.74 mmol) are added and the mixture is stirred for 10 min. Then B-1 (70 mg, 0.25 mmol) is added and the reaction is stirred at RT for 3 h. The mixture is purified by preparative LCMS (using a solvent gradient $H_2O$/ACN with $NH_4OH$). After concentration the residue is extracted with DCM. The organic phase is dried and concentrated to afford 70 mg of compound Example 3. ESI-MS: 454 [M+Na]$^+$; HPLC (Rt): 3.52 min (method H).

The following examples are prepared in analogy to the above described procedure using the corresponding acid (see Acid Intermediates) and amine (see Amine Intermediates) as described before, adjusting reaction time: overnight for Example 14, 19:

| Example | Structure | ESI-MS [M + H]$^+$ | HPLC (Rt) [min] | HPLC Method |
|---|---|---|---|---|
| 14 | [structure] | 435 | 3.31 | H |

| Example | Structure | ESI-MS [M + H]+ | HPLC (Rt) [min] | HPLC Method |
|---|---|---|---|---|
| 19 | 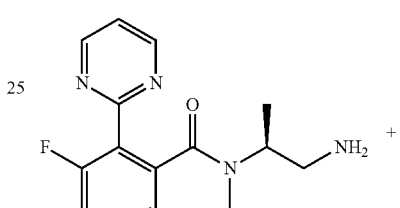 | 430 | 3.66 | H |

Example 6

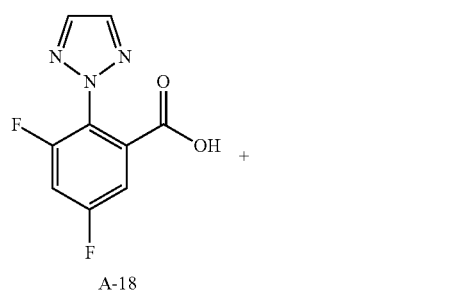

Example 11

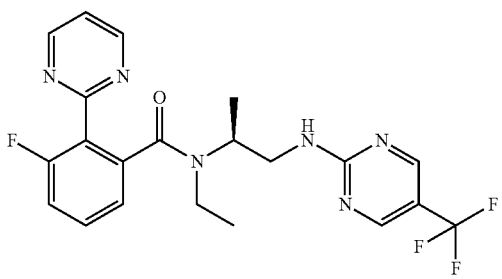 [SMILES: CCN(C(=O)c1ccc(F)cc1-c1ncccn1)[C@@H](C)CNc1ncc(C(F)(F)F)cn1]

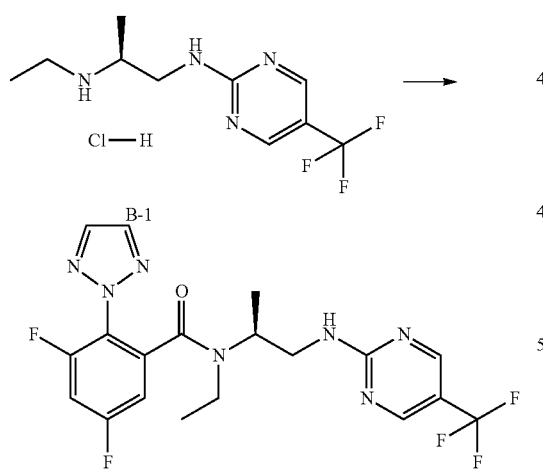

A-18 (640 mg, 2.8 mmol), B-1 (809 mg, 2.84 mmol), CIP (1.0 g, 3.7 mmol) and DIPEA (1.5 mL, 8.5 mmol) are mixed in dry ACN (3 mL) and the mixture is stirred at RT overnight. The mixture is concentrated and the residue is taken up with EA and washed with citric acid (10% aq. solution), Na₂CO₃ (aq. solution) and brine, dried and concentrated. The residue is purified by flash column chromatography on silica gel (using a solvent gradient from cyclohexane to cyclohexane/EA 2/3) to afford 802 mg of Example 6. ESI-MS: 456 [M+Na]+; HPLC (Rt): 4.40 min (method N).

To a stirred mixture of C-1 (1.0 g, 3.3 mmol) in NMP (15 mL), 11.1 (700 mg, 3.8 mmol) and DIPEA (0.70 mL, 4.1 mmol) are added at RT under a nitrogen atmosphere. The reaction is heated at 100° C. for 1 h. After cooling the reaction is poured into water an extracted with EA. The organic layer is separated, washed with citric acid (10% aq. solution), dried and concentrated. The residue is purified by flash column chromatography on silica gel (using as eluent DCM/MeOH 97/3) to afford 1.3 g of Example 11. ESI-MS: 471 [M+Na]+; HPLC (Rt): 3.16 min (method H).

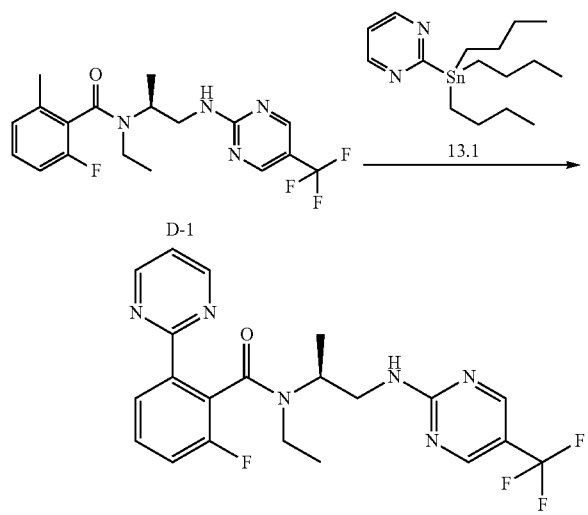

D-1

Example 13

To a mixture of D-1 (160 mg, 0.29 mmol), CuI (2.80 mg, 0.01 mmol), Pd(PPh$_3$)$_4$ (17 mg, 0.01 mmol) and CsF (66 mg, 0.44 mmol) in dry DME (2.0 mL) under a nitrogen atmosphere is added 13.1 (92 µl, 0.29 mmol). The reaction is heated to 120° C. by microwave for 2 h. Then to 130° C. for 30 min. After cooling, the mixture is poured into water and extracted with Et$_2$O (2×). The organic layer is dried and concentrated to give the crude product which is purified by preparative LCMS (using a solvent gradient H$_2$O/ACN with NH$_4$OH) to afford 28 mg of Example 13. ESI-MS: 471 [M+Na]$^+$; HPLC (Rt): 3.54 min (method H).

Example 15

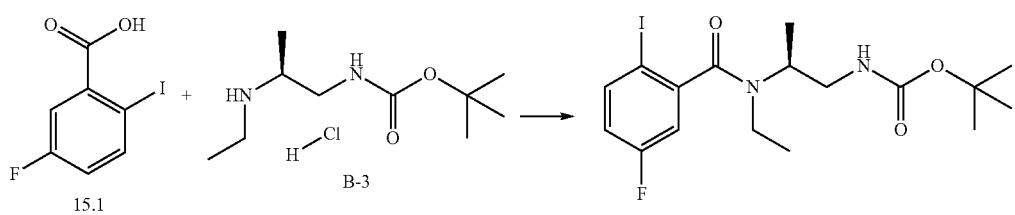

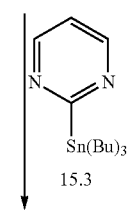

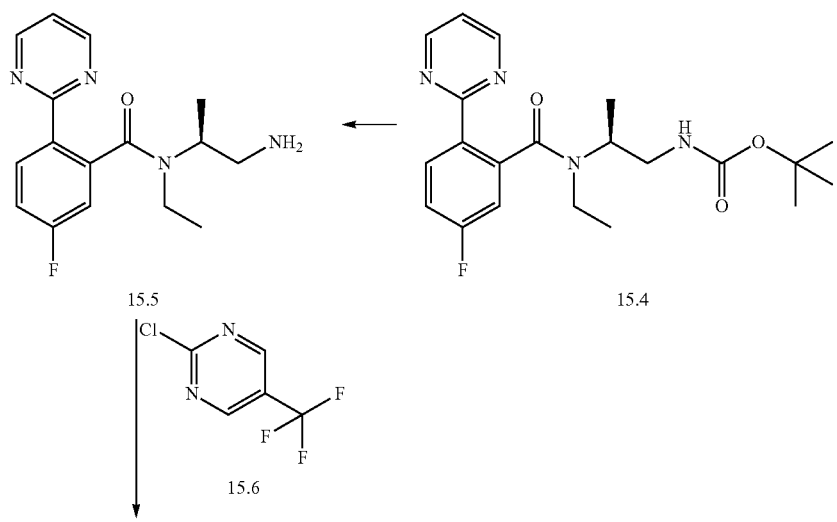

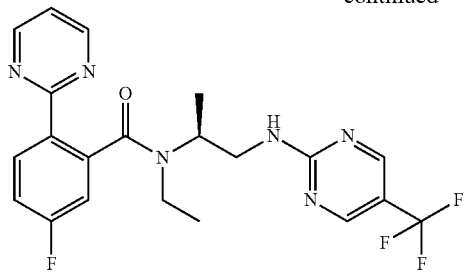

Example 15

Step 1: 15.1 (1.50 g, 5.64 mmol) is dissolved in DCM (8.3 mL). Then oxalylchloride (5.6 mL, 11.3 mmol) is added followed by one drop of DMF and the mixture is stirred at RT for 1 h. The solvent is removed under reduced pressure. The residue is mixed with DCM (8 mL) and added at 0° C. to a mixture of B-3 (1.04 g, 5.13 mmol) and DIPEA (3.9 mL, 22.6 mmol) in DCM (8 mL). The mixture is stirred for 12 h at 20° C. Water is added and the organic layer and washed with NH$_4$Cl (sat. aq. solution), KHCO$_3$ (sat. aq. solution) and water. The organic phase is dried and concentrated. The residue is purified by flash column chromatography (using a solvent gradient from 100% Cyclohexane to Cyclohexane/EA 8/2) to afford 0.91 g of 15.2. ESI-MS: 451 [M+H]$^+$; HPLC (Rt): 1.17 min (method P).

Step 2: 15.2 (914 mg, 1.93 mmol), 15.3 (980 µL, 3.09 mmol), CuI (36.7 mg, 0.19 mmol) CsF (589 mg, 3.88 mmol) and Pd(PPh$_3$)$_4$ are dissolved in dry DMF (7.0 mL) and the mixture is stirred in a microwave at 130° C. for 15 min. Water is added and the product is extracted with EA. The organic phase is dried and concentrated. The crude product is purified by flash column chromatography on silica gel (using a solvent gradient from cyclohexane/EA 30/70 to 100% EA) to afford 477 mg of 15.4. ESI-MS: 403 [M+H]$^+$; HPLC (Rt): 1.02 min (method P).

Step 3: To a mixture of 15.4 (477 mg, 1.19 mmol) in MeOH (6.0 mL) HCl (4M aq. solution, 7.41 mL, 29.6 mmol) is added at 0° C. The mixture is stirred at RT for 1 h. The solvent is evaporated and the residue is purified by prep. HPLC-MS (using a solvent gradient H$_2$O/ACN with NH$_4$OH) to afford 333 mg of 15.5. ESI-MS: 303 [M+H]$^+$; HPLC (Rt): 2.98 min (method N).

Step 4: To a mixture of 15.5 (45.0 mg, 0.15 mmol) in dry DMF (1.0 mL) DIPEA (77.3 µL, 0.45 mmol) is added. After 20 min 15.6 (32.6 mg, 0.18 mmol) is added and the mixture is stirred at 70° C. for 1.5 h. EA is added and the organic layer is washed with water, dried and concentrated. The residue is purified by flash column chromatography on silica gel (using a solvent mixture of cyclohexane/EA 10/90) to afford 34 mg of Example 15. ESI-MS: 471 [M+Na]$^+$; HPLC (Rt): 3.21 min (method H).

Example 17

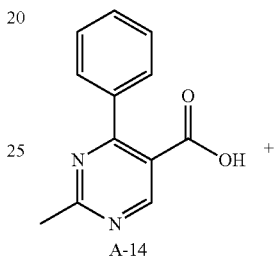

A-14

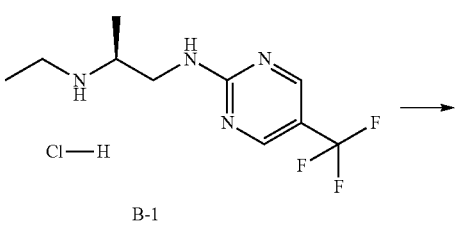

B-1

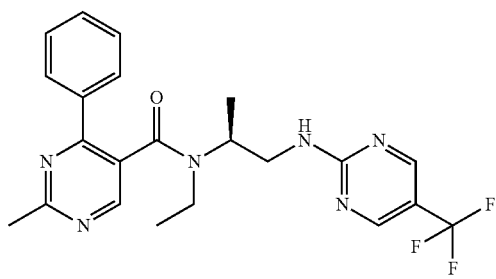

Example 17

To a mixture of A-14 (135 mg, 0.63 mmol), B-1 (150 mg, 0.53 mmol) and DIPEA (273 µL, 1.60 mmol) in dry ACN (2.0 mL) is added CIP (191 mg, 0.68 mmol) and the mixture is stirred at RT for 2 days. ACN/H$_2$O is added and the mixture is purified by prep. HPLC-MS (using a solvent gradient H$_2$O/ACN with NH$_4$OH) to afford 133 mg of Example 17. ESI-MS: 445 [M+Na]$^+$; HPLC (Rt): 1.04 min (method G).

Example 18

Example 22

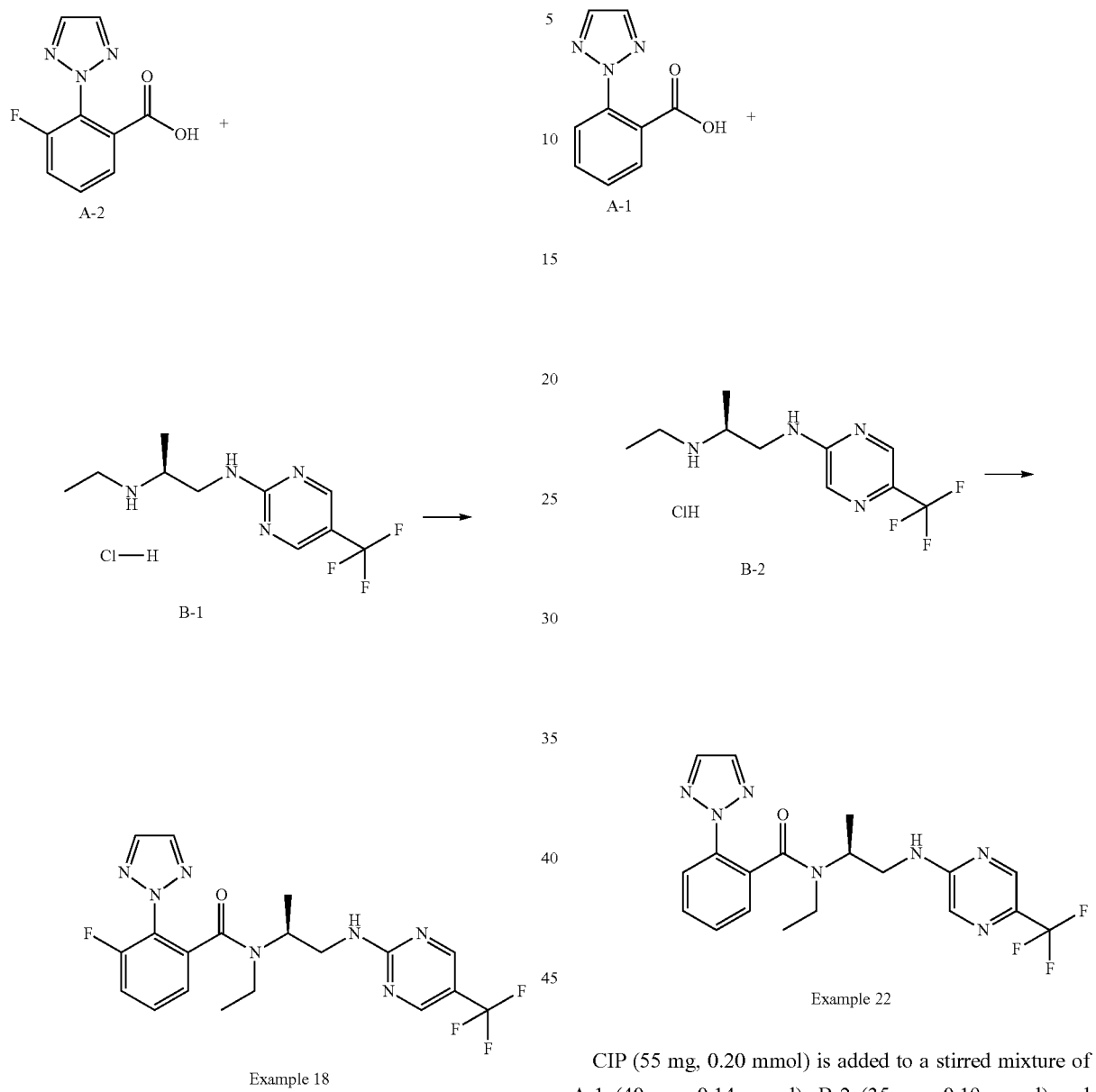

Example 18

Thionylchloride (0.28 mL, 3.86 mmol) is added to a stirred mixture of A-2 (800 mg, 3.86 mmol) in toluene (6.0 mL). A drop of DMF is added and the mixture is heated at 60° C. for 2 h. The solvent is evaporated. The residue is dissolved in dry DCM (10 mL) and then a mixture of B-1 (1.00 g, 3.50 mmol) and TEA (1.5 mL, 11 mmol) in DCM is added dropwise at 0° C. The reaction mixture is warmed at RT. Water is added and the organic layer is dried and concentrated. The crude product is purified by flash column chromatography on silica gel (using a solvent mixture of EA/n-hexane/MeOH 90/10/1) to afford 1.2 g of Example 18. ESI-MS: 438 [M+Na]$^+$; HPLC (Rt): 4.32 min (method T).

CIP (55 mg, 0.20 mmol) is added to a stirred mixture of A-1 (40 mg, 0.14 mmol), B-2 (35 mg, 0.19 mmol) and DIPEA (80 µL, 0.47 mmol) in dry DMA (2.0 mL) at RT. After 16 h the reaction is treated with water and extracted with EA. Organic layer is separated and washed with NaHCO$_3$ (5% aq. solution). The organic layer is separated, dried and concentrated. The residue is purified by flash column chromatography on silica gel (using as eluent DCM/MeOH 100/2) to afford 35 mg of Example 22. ES+/−: 420 [M+H]$^+$; HPLC (Rt): 4.28 min (method N).

The following examples are prepared in analogy to the above described procedure using the corresponding acid (see Acid Intermediates) and amine (see Amine Intermediates) as described before.

| Example | Structure | ESI-MS [M + H]+ | HPLC (Rt) [min] | HPLC Method |
|---|---|---|---|---|
| 23 | 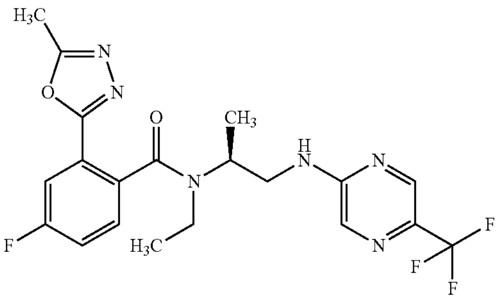 [SMILES: CCN(C(=O)c1ccc(F)cc1-c1nnc(C)o1)[C@@H](C)CNc1cnc(C(F)(F)F)cn1] | 453 | 3.26 | H |

Example 24

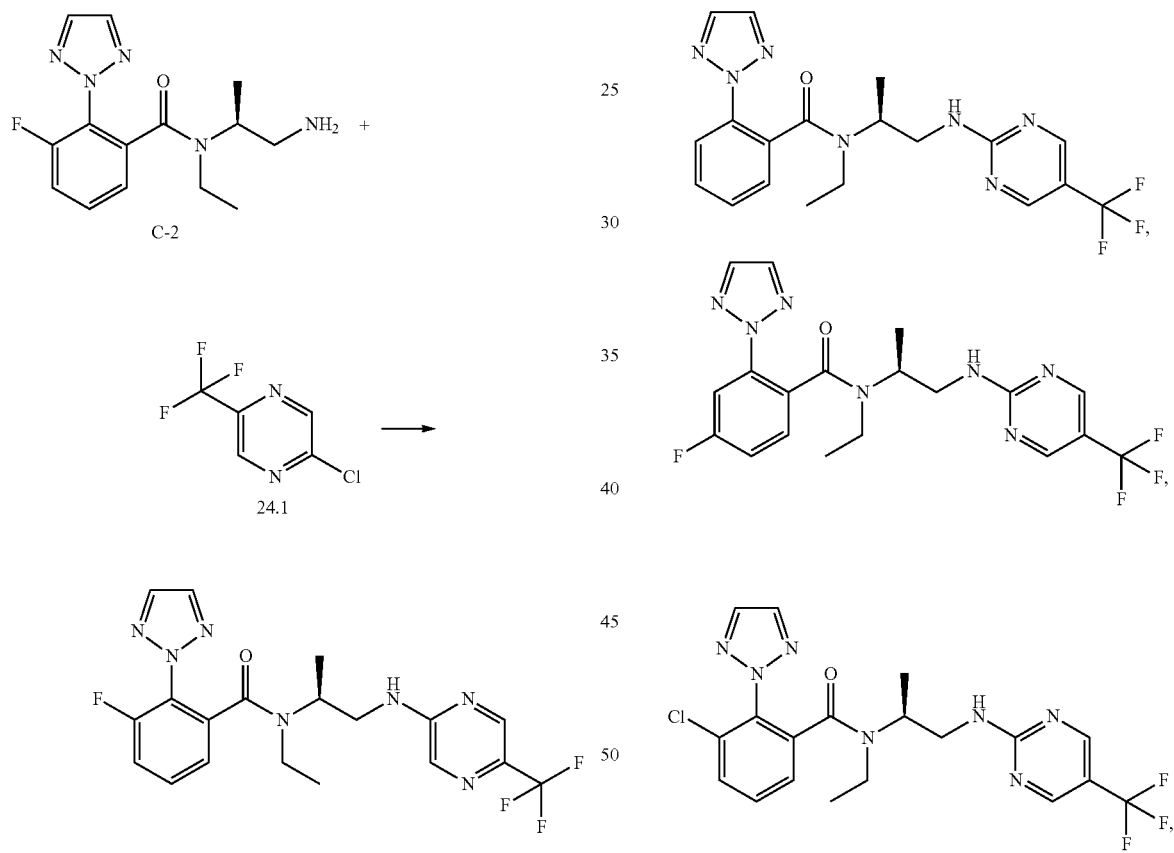

Example 24

To a mixture of C-2 (30.0 mg, 0.08 mmol) and DIPEA (35.0 μL, 0.21 mmol) in DMF (4.0 mL) is added 24.1 (18.0 mg, 0.10 mmol) under a nitrogen atmosphere. The reaction mixture is heated in the microwave at 90° C. for 30 min. After cooling the reaction mixture, water is added and the mixture is extracted with DCM, the combined organic phases are washed with NH4Cl (sat. aq. solution), dried and concentrated. The crude product is purified by preparative LCMS (using a solvent gradient H₂O/ACN with HCOOH) to afford 10 mg of Example 24. ESI-MS: 438 [M+H]+; HPLC (Rt): 4.42 min (method N).

The invention claimed is:
1. A compound selected from the group consisting of

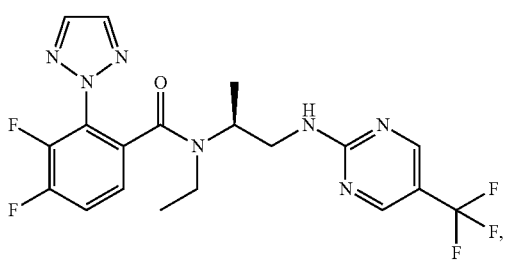

75
-continued
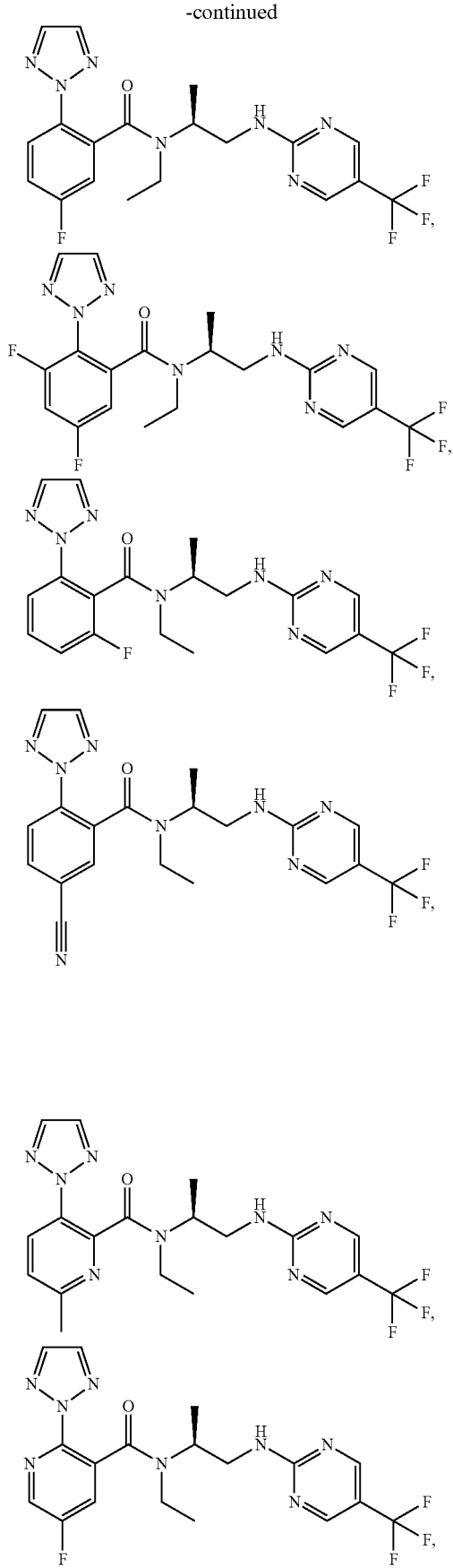
76
-continued
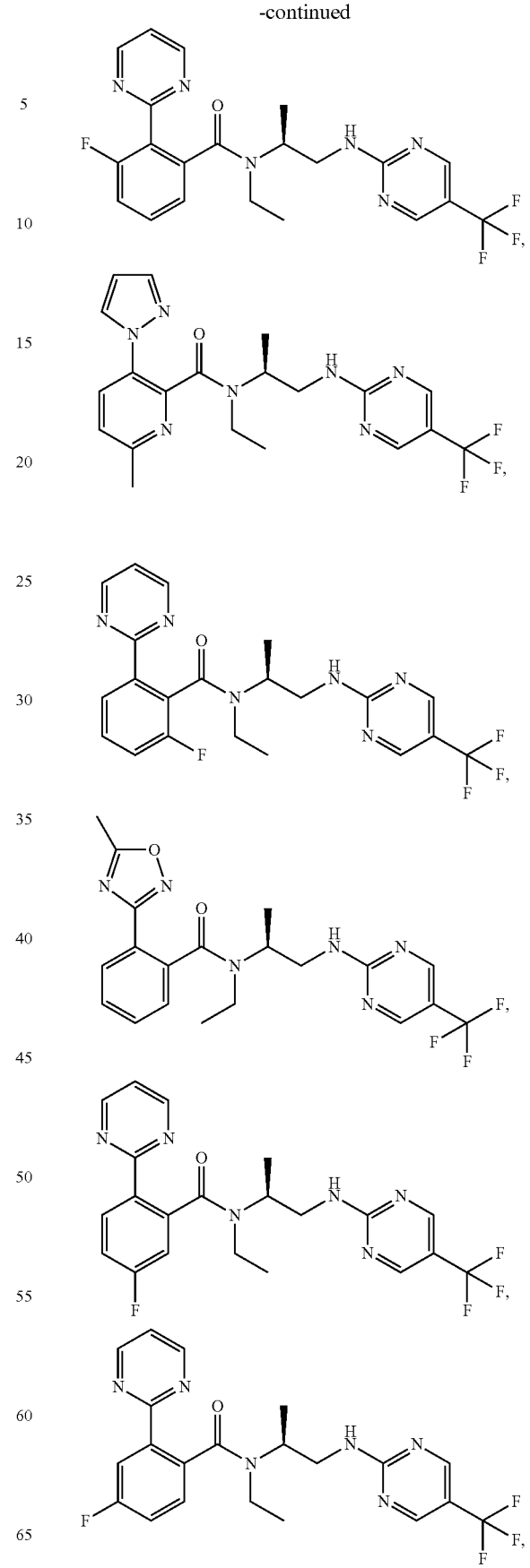

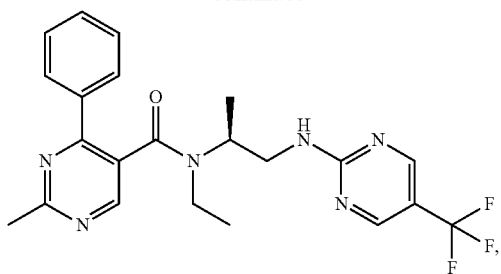
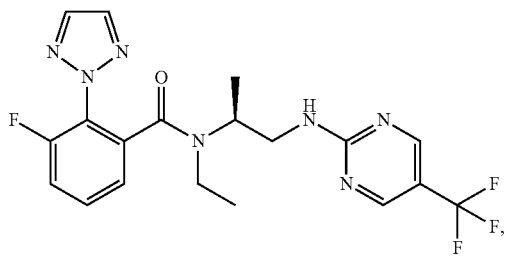 [SMILES: CCN(C(=O)c1cccc(F)c1-n1nccn1)[C@@H](C)CNc1ncc(C(F)(F)F)cn1]
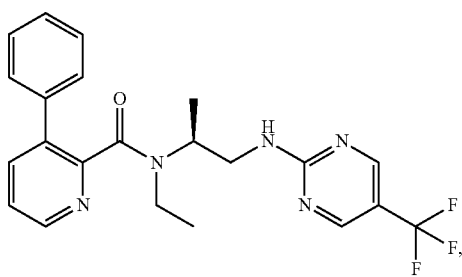
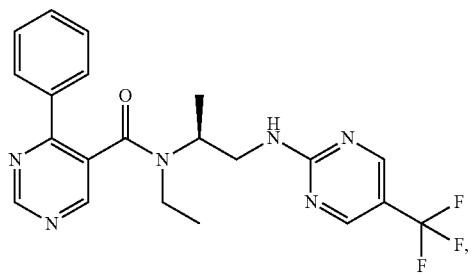
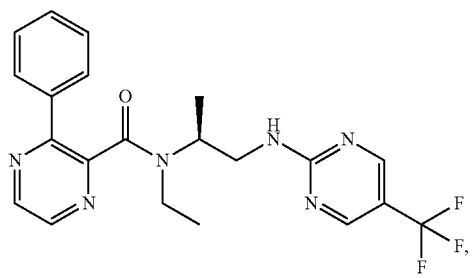
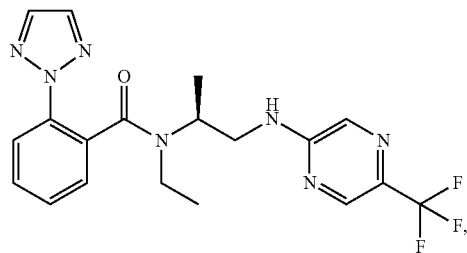
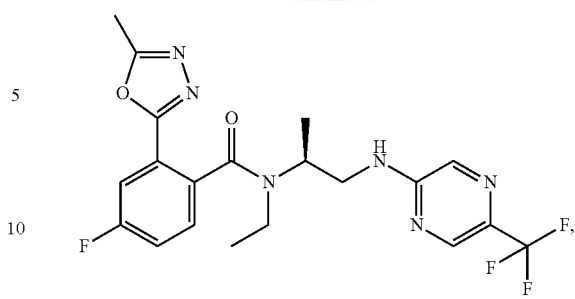
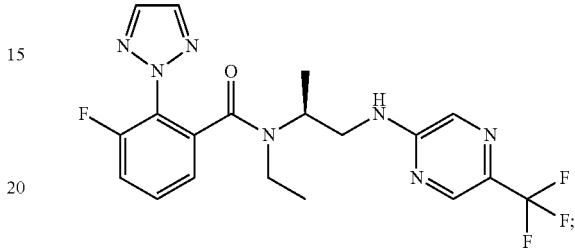
or a salt thereof, particularly a pharmaceutically acceptable salt thereof.
2. The compound according to claim 1, selected from the group consisting of
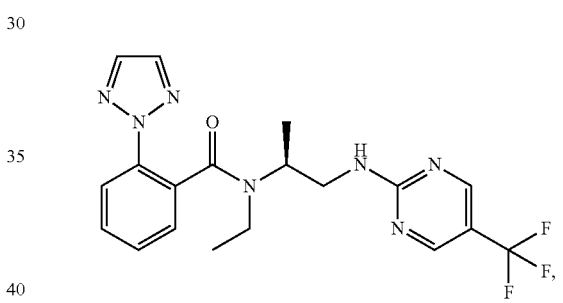
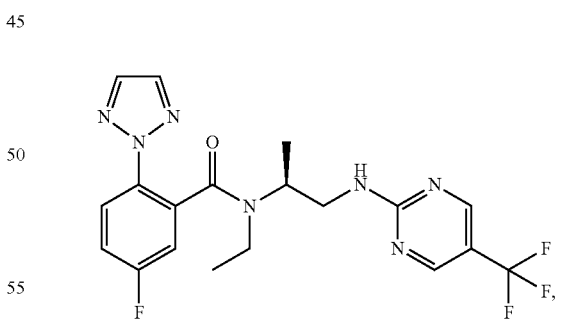
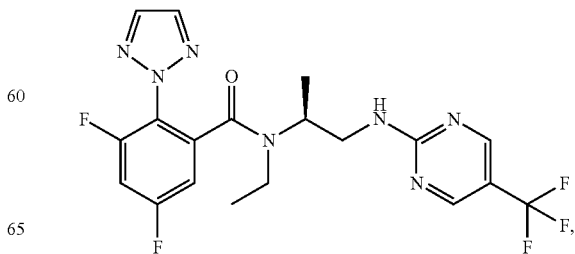

-continued

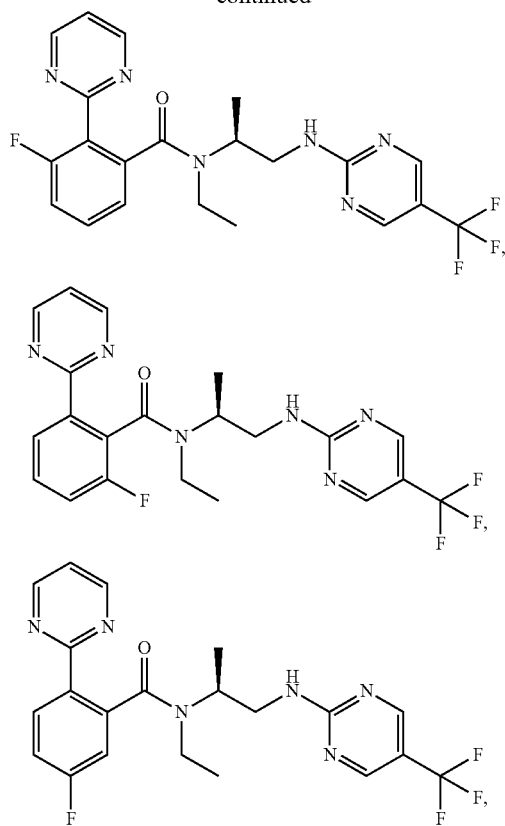

-continued

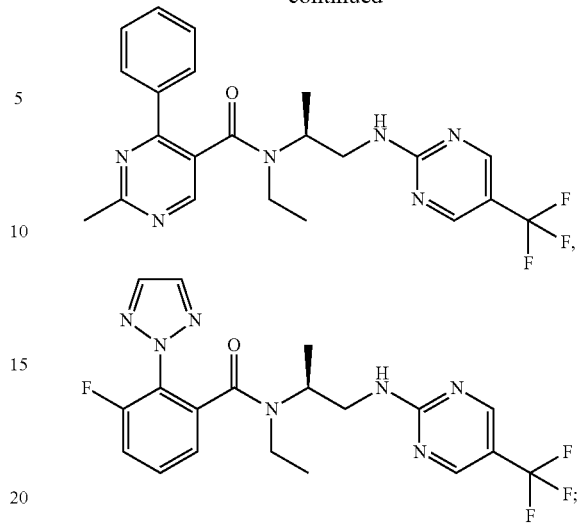

or a salt thereof, particularly a pharmaceutically acceptable salt thereof.

3. A pharmaceutical composition comprising the compound according to claim 1 or a pharmaceutically acceptable salt thereof in admixture with a pharmaceutically acceptable adjuvant, diluent and/or carrier.

4. A method of treating a disease comprising administering a compound of claim 1 or a pharmaceutically acceptable salt thereof to a patient in need thereof wherein the disease is a psychiatric or neurological condition associated with impulse control deficits.

* * * * *

UNITED STATES PATENT AND TRADEMARK OFFICE
CERTIFICATE OF CORRECTION

PATENT NO. : 9,884,854 B2  
APPLICATION NO. : 15/485262  
DATED : February 6, 2018  
INVENTOR(S) : Doris Riether et al.

Page 1 of 1

It is certified that error appears in the above-identified patent and that said Letters Patent is hereby corrected as shown below:

On the Title Page

In the title and in the Specification, at Column 1, Lines 2-4 delete:
"N-[(Pyrimidinylamino)Propanyl]-And N[(Pyrazinylamino)Proppanyl]Arylcarboxamides"
And insert:
-- N-[(Pyrimidinylamino)Propanyl]-And N[(Pyrazinylamino)Propanyl]Arylcarboxamides --

Signed and Sealed this  
Third Day of April, 2018

Andrei Iancu  
*Director of the United States Patent and Trademark Office*